United States Patent [19]

Miller et al.

[11] Patent Number: 5,852,204
[45] Date of Patent: Dec. 22, 1998

[54] PYRROLO[3,2-B-]-CARBAZOLES AND 1H[1] BENZOTHIENO [2,3-F] INDOLES HAVING ANTI-TUMOR ACTIVITY

[75] Inventors: David Drysdale Miller; Sadie Vile, both of Stevenage; Patrick Vivian Richard Shannon, Penarth, all of United Kingdom; Laddawan Chunchatprasert, Khon Kaen, Thailand; Alan Thomas Hudson, Otford, United Kingdom

[73] Assignee: University College Cardiff Consultants Limited, United Kingdom

[21] Appl. No.: 687,347

[22] PCT Filed: Jan. 31, 1995

[86] PCT No.: PCT/GB95/00190

§ 371 Date: Aug. 16, 1996

§ 102(e) Date: Aug. 16, 1996

[87] PCT Pub. No.: WO95/21170

PCT Pub. Date: Aug. 10, 1995

[30] Foreign Application Priority Data

Jan. 2, 1994 [GB] United Kingdom .................... 9401921

[51] Int. Cl.⁶ ...................... C07D 487/04; C07D 495/04; A61K 31/40; A61K 31/695; C07F 7/10; C07H 9/04

[52] U.S. Cl. .......................... 548/421; 514/410; 536/1.11; 536/4.1; 548/426

[58] Field of Search ...................................... 548/421, 426; 536/4.1, 1.11; 514/410

[56] References Cited

U.S. PATENT DOCUMENTS

| | | | |
|---|---|---|---|
| 3,873,528 | 3/1975 | Kuhlthau | 548/421 |
| 4,021,451 | 5/1977 | Dobson et al. | 548/421 X |
| 4,362,739 | 12/1982 | Kuehne | 548/421 X |

FOREIGN PATENT DOCUMENTS

| | | | |
|---|---|---|---|
| 0447703 | 9/1991 | European Pat. Off. | 548/421 |
| 0830223 | 3/1960 | United Kingdom | 548/421 |
| 94/02483 | 2/1994 | WIPO | 548/421 |

Primary Examiner—Floyd D. Higel
Attorney, Agent, or Firm—Nixon & Vanderhye

[57] ABSTRACT

The present invention relates to heterocyclic compounds which have been found to have anti-tumor activity. More specifically, the invention concerns pyrrolo[3,2-b]carbazoles and 1H-[1] benzothieno [2,3-f] indoles, methods for their preparation, pharmaceutical formulations containing them and their use as anti-tumor agents. The compounds have low toxicity against normal cell lines while exhibiting anti-tumor cell activity.

7 Claims, No Drawings

PYRROLO[3,2-B-]-CARBAZOLES AND 1H[1] BENZOTHIENO [2,3-F] INDOLES HAVING ANTI-TUMOR ACTIVITY

The present invention relates to heterocyclic compounds which have been found to have anti-tumour activity. More specifically, the invention concerns pyrrolo[3,2-b]-carbazoles and 1H-[1] benzothieno[2,3-f]indoles, methods for their preparation, pharmaceutical formulations containing them and their use as anti-tumour agents.

Research in the area of cancer chemotherapy has produced a variety of anti-tumour agents, which have differing degrees of efficacy. Standard clinically used agents include adriamycin, actinomycin D, methotrexate, 5-fluorouracil, cis-platinum, vincristine and vinblastine. However, these presently available anti-tumour agents are known to have various disadvantages, such as toxicity to healthy cells and resistance to certain tumour types.

Thus, there thus exists a continuing need to develop new and improved anti-tumour agents.

Khoshtariya et al, khim Geterotsikl Soedin (1980), (2) 203–8 and (1984), (10) 1366–70, disclose the synthesis of certain indolobenzo[b]thiophenes and indolobenzo[b]furans respectively.

Kakhabrishvili et al, khim Geterotsikl Soedin (1985), (3) 355–8 disclose the synthesis of certain derivatives of indolo [5,6-d] and indolo [5,4-d] benzo[b] furans.

The patent specification EP447,703 discloses the synthesis of certain benzo[5,6-b]benzofuran-2-carboxylates. Copending PCT application WO9301512 discloses certain pyrrolo [3,2-b]carbazoles, 1H-benzofuro [3,2-f] indoles and 1H-(1) benzothieno [2,3-f] indoles having antitumour activity.

L. Chunchatprasert et al, J. Chem. Soc., Perkin Trans I, 1779 (1992) disclose the synthesis of pyrrolo[3,2-b] carbazoles, 1H-benzofuiro[3,2-f]indoles and 1H-[1] benzothieno[2,3-f]indoles.

There have now been discovered a further group of novel compounds which exhibit anti-tumour cell activity with low toxicity against normal cell lines.

Thus, in a first aspect the present invention provides a compound of the general formula (1)

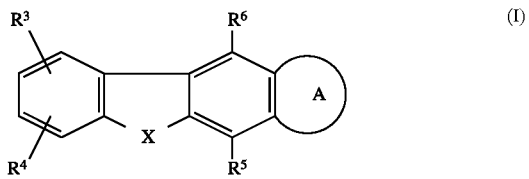

and salts and physiologically functional derivatives thereof, wherein A is

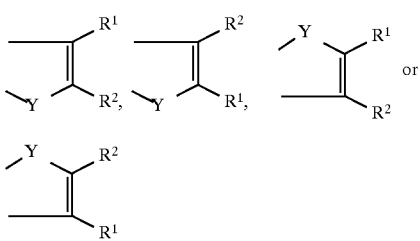

X is O, S, SO, $SO_2$, $CH_2$, CO or $NR^7$, wherein $R^7$ is H, alkyl, aralkyl, aryl, alkenyl, acyl, alkynyl, sulphonyl or substituted sulphonyl;

Y is O, S, SO, $SO_2$, $CH_2$, CO or $NR^7$, with the proviso that Y is not O when X is O;

$R^1$ is $COOR^8$, $CONHR^8$, $CONR^8R^9$, $CSOR^8$, $CSSR^8$, $COSR^8$, $CSNHR^8$, $CSNR^8 R^9$, $CNHOR^8$ wherein $R^8$ and $R^9$ are independently $C_{1-10}$ optionally substituted hydrocarbyl group which may optionally contain one or two oxygen atoms in the chain; or $R^8$ and $R^9$ are independently alkoxyalkyl, heterocycloalkyl, heteroaralkyl, or $R^8$ and $R^9$ are a sugar group;

with the proviso that $R^1$ is not $COOR^8$, $CONHR^9$, $CONR^9R^{10}$, wherein $R^8$ is alkyl, aryl, aralkyl or aryl substituted by one or more alkyl, alkoxy, halo, sulphinyl, amino (optionally substituted by one or two alkyl groups), haloalkyl, sulphonyl and cyano, $R^9$ and $R^{10}$ are independently alkyl or aryl;

$R^2$ is H, halo, cyano, $COOR^8$, alkyl, aryl, alkenyl, alkynyl, alkoxy, (wherein alkyl, aryl, alkenyl, alkynyl and alkoxy can be substituted) or $CH_2CH_2CO_2R^{12}$ wherein $R^{12}$ is alkyl or aryl;

$R^3$ and $R^4$ are independently H, hydroxy, alkyl, haloalkyl, alkoxy, halo, cyano, nitro, amino, alkyl amino, dialkyl amino, substituted alkyl, carboxyl or $CO_2R^{12}$;

$R^5$ is H, hydroxy, aryloxy, aralkyloxy, alkyl, substituted alkyl, aralkyl, nitro, amino, halo, cyano or CHO; and $R^6$ is H, aryl, alkyl, aralkyl, nitro, halogen, CHO or $COR^{13}$ wherein $R^{13}$ is alkyl or aryl.

The term hydrocarbyl includes straight-chain or branched alkyl, alkenyl and alkynyl groups; cycloalkyl, cycloalkenyl and cycloalkynyl groups; and aralkyl, aralkenyl and aralkynyl groups where the alkyl, alkenyl or alkynyl portion may be straight-chain or branched.

Alkyl groups present in general formula (I) may be straight or branched chain alkyl groups, and may contain 1–10 carbon atoms and suitably 1–6 carbon atoms. Examples of such alkyl groups include methyl, ethyl, t-butyl and the like.

Acyl groups may be straight or branched and may contain 1–10 carbon atoms and suitably 1–6 carbon atoms. Examples of suitable acyl groups include ethanoyl and propanoyl groups.

Alkoxy may be straight or branched and may contain 1–10 carbon atoms and suitably 1–6 carbon atoms. Examples of suitable alkoxy groups include methoxy, ethoxy and the like.

Aryl includes both carbocyclic aryl groups and heterocyclic aryl groups normally containing a maximum of 10 ring atoms. Carbocyclic aryl groups include, eg phenyl and naphthyl and contain at least one aromatic ring. Heterocyclic aryl groups include eg thienyl, furyl, pyridyl, indole and quinoline rings.

An aralkyl group may contain from 1 to 4 atoms in the alkyl portion and the aryl portion may be a carbocyclic or heterocyclic aryl group.

When $R^8$ and $R^9$ are independently optionally substituted $C_{1-10}$ hydrocarbyl which may optionally contain one or two oxygen atoms in the chain this includes substituted alkyl, hydroxyalkyl, alkenyl, alkynyl, carbamoylalkyl, alkoxyalkyl, cycloalkyl, cycloalkenyl, aralkyl, aryloxyalkyl.

Cycloalkyl includes both cycloalkyl groups and heterocyclo alkyl groups normally containing between 3 and 6 ring atoms. Heterocycloalkyl groups include e.g. morpholino, thiomorpholino, piperidino, imidazolino, pyrrolidino, pyrazolidino, piperazino, tetrahydrofuranyl, tetrahydropyranyl. Cycloalkyl groups include e.g. cyclopentyl, cyclohexyl, etc.

Substituents which may be present on the $C_{1-10}$ hydrocarbyl group may optionally containing one or two oxygen atoms in the chain include hydroxy, azido, alkenyl, halo, hydroxy, nitro ($NO_2$), amino, alkylamino (optionally substituted by one or 2 alkyl groups), cyano, carboxylate, alkyl ester, aralkyl esters, aryl ester (wherein the alkyl ester, aralkyl ester and aryl ester can be substituted) alkyl, aryl, aralkyl, aryloxy, arylalkoxy, substituted arylalkoxy, sulphinyl, sulphonyl, thio, alkylthio, alkoxy, hydroxyalkyl, halo alkyl, phosphate, phosphonate, silyl, silyloxy, (wherein silyl and silyloxy may be substituted by one or more $C_{1-6}$ alkyl or aryl) keto, formyl. Substituents which may be present on alkyl esters, aralkyl esters and aryl esters include nitro, amino, hydroxy, alkoxy, halogen, cyano and alkyl.

Where $R^8$ is a sugar this group may be present in a protected or unprotected form. Preferred sugar-protecting groups include isopropylidene, benzylidene acetate, benzoyl, paranitrobenzyl, paranitrobenzoyl, benzyl, substituted silyl and tetrahydropyranyl.

When $R^8$ is a sugar such as a tetrose, pentose, hexose (including furnanose and pyranose) or heptose, preferred sugars include glucose, fructose, mannose, ribose, arabinose.

Substituents which may be present on the sulphonyl and sulphinyl groups include alkyl, aryl and aralkyl.

Halogen represents fluoro, chloro, bromo or iodo.

Preferred compounds have the formula (VI)

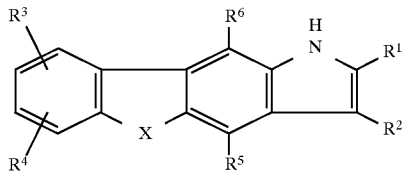

wherein,

X preferably represents S, O or NH;

$R^1$ is preferably $COOR^8$, with $R^8$ preferably being a group of formula

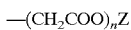

where n is 0 or 1 and

Z is a phenyl or benzyl group optionally substituted by one or more groups selected from hydroxy, carboxyl, nitro, amino, phthalimido, p-nitrobenzyl and p-nitrobenzyloxy;

or Z is a $C_{1-4}$ straight or branched alkyl or cycloalkyl group optionally substituted by one or more groups selected from hydroxy, carboxyl, halo, amino, dialkylamino, alkylsulphinyl, alkylsulphonyl and benzyloxy;

or Z is a substituted glucofuranosyl moiety;

$R^2$ is preferably H or alkyl;

$R^3$ is preferably H, alkoxy, hydroxy or halo;

$R^4$ is preferably H, alkoxy, hydroxy or halo;

$R^5$ is preferably alkyl; and $R^6$ is preferably H, and salts and physiologically functional derivatives thereof.

Particularly preferred compounds according to the present invention include:

and physiologically functional derivatives thereof

[(2-Dimethylamino)ethyl] 3,4-dimethylpyrrolo[3,2-b]carbazole-2-carboxylate (2-Methylsulphonylethyl) 3,4-dimethylpyrrolo[3,2-b]carbazole-2-carboxylate (2-Methylsulphinylethyl) 3,4-dimethylpyrrolo[3,2-b]carbazole-2-carboxylate (1,3-Dibenzyloxypropyl-2) 3,4-dimethylpyrrolo[3,2-b]carbazole-2-carboxylate (1-Benzyloxy-3-hydroxypropyl-2) 3,4-dimethylpyrrolo[3,2-b]carbazole-2-carboxylate (1,3-Dihydroxypropyl-2) 3,4-dimethyl-pyrrolo[3,2-b]carbazole-2-carboxylate (2-Amino-2-methylpropyl-1) 3,4-dimethylpyrrolo[3,2-b]carbazole-2-carboxylate (4-Nitrophenylmethyl) 2-(3,4-dimethylpyrrolo[3,2-b]carbazole-2-carboxy)acetate 2-(3,4-Dimethylpyrrolo[3,2-b]carbazole-2-carboxy) acetic acid Cyclohexyl 3,4-dimethylpyrrolo[3,2-b]carbazole-2-carboxylate Cyclohexylmethyl 3,4-dimethylpyrrolo[3,2-b]carbazole-2-carboxylate Cyclopentyl 3,4-dimethylpyrrolo[3,2-b]carbazole-2-carboxylate Cyclooctyl 3,4-dimethylpyrrolo[3,2-b]carbazole-2-carboxylate 3,5-Di(tert-butyldiphenylsilyloxy)cyclohexyl 3,4-dimethylpyrrolo[3,2-b]carbazole-2-carboxniate 3,5-Dihydroxycyclohexyl 3,4-dimethylpyrrolo[3,2-b]carbazole-2-carboxylate cis-4-tert-Butyldiphenylsilyloxycyclohexyl 3,4-dimethylpyrrolo[3,2-b]carbazole-2-carboxylate cis-4-Hydroxycyclohexyl 3,4-dimethylpyrrolo[3,2-b]carbazole-2-carboxylate trans4-tert-Butyldiphenylsilyloxycyclohexyl 3,4-dimethylpyrrolo[3,2-b]carbazole-2-carboxylate trans-4-Hydroxycyclohexyl 3,4-dimethylpyrrolo[3,2-b]carbazole-2-carboxylate Tetrahydro-2H-pyran-4-yl 3,4-dimethylpyrrolo[3,2-b]carbazole-2-carboxylate 1-Benzylpiperidin-4-yl 3,4-dimethylpyrrolo[3,2-b]carbazole-2-carboxylate Piperidin-4-yl 3,4-dimethylpyrrolo[3,2-b]carbazole-2-carboxylate 1-Methylpiperidin4-yl 3,4-dimethylpyrrolo[3,2-b]carbazole-2-carboxylate (3,4-Dirnethylpyrrolo[3,2-b]2-carbazolyl)3-O-(1,2:5,6-di-O-isopropylideneglucofuranoside)

(3,4-Dimethylpyrrolo[3,2-b]2-carbazolyl) 3-O-(1,2-O-isopropyl-ideneglucofiranoside)

[3-(4-Nitrophenylmethoxy)phenyl] 3,4-dimethylpyrrolo[3,2-b]carbazole-2-carboxylate (3-Hydroxyphenyl) 3-4,-dimethylpyrrolo[3,2-b]carbazole-2-carboxylate (4-Phthalamidophenyl) 3,4-dimethylpyrrolo[3,2-b]carbazole-2-carboxylate 4-(Aminophenyl) 3,4-dimethylpyrrolo[3,2-b]carbazole-2-carboxylate (4-Nitrophenylmethyl) 3-(3,4-dimethylpyrrolo[3,2-b]carbazole-2-carboxy)benzoate 3-(3,4-Dimethylpyrrolo[3,2-b]carbazole-2-carboxy) benzoic acid 3-(tert-Butyldiphenylsilyloxymethyl)phenyl 3,4-dimethylpyrrolo[3,2-b]carbazole-2-carboxylate (3-Hydroxymethyl)phenyl 3,4-dimethylpyrrolo[3,2-b]carbazole-2-carboxylate

[3-(4-Nitrophenylmethoxy)phenyl] 4-methyl-1H-[1]benzothieno[2,3-f]indole-2-carboxylate (3-Hydroxyphenyl)4-methyl-1H-[1]benzothieno[2,3-f]indole-2-carboxylate 3-(4-Nitrophenylmethoxy)phenylmethyl 3,4-dimethylpyrrolo[3,2-b]carbazole-2-carboxylate 3-(tert-Butyldiphenylsilyloxyphenyl)methyl 3,4-dimethylpyrrolo[3,2-b]carbazole-2-carboxylate (3-Hydroxyphenyl)methyl 3,4-dimethylpyrrolo[3,2-b]carbazole-2-carboxylate (1-Hydroxy-3-methylpropyl-2) 3,4-dimethylpyrrolo[3,2-b]carbazole-2-carboxamide 2-Hydroxyethyl 3,4-dimethylpyrrolo[3,2-b]carbazole-2-carboxamide 2-Chloroethyl 3,4-dimethylpyrrolo[3,2-b]carbazole-2-carboxamide N-(2-Arainoethyl) 3,4-dimethylpyrrolo[3,2-b]carbazole-2-carboxamide N-(2-Acetamidoethyl) 3,4-dimethylpyrrolo[3,2-b]carbazole-2-carboxamide (3-Aminopropyl-1) 3,4-dimethylpyrrolo[3,2-b]carbazole-2-carboxamide 2-Hydroxyethyl 4-methyl-1H-[1]benzothieno[2,3-f]indole-2-carboxamide 2-Chloroethyl 4-methyl-1H-[1]benzothieno[2,3-f]indole-2-carboxamide Compounds of the general formula (I) have been tested against two specially developed cell lines which are clones of the human fibrosarcoma cell-line, HT1080. One clone, HT1080scc2, retains the transformed phenotype of the parental line, whilst the other, HT10801c, is a morphologically flat, non-tumourigenic, revertant.

Thus, the effects of potential anti-tumour compounds can be evaluated on the basis of their ability to effect detransformation in HT1080scc2 cells.

Compounds of the present invention have been found to be particularly effective in this assay system.

The compounds also exhibit low toxicity against normal cells.

Compounds of the formula (I) may be prepared by the acid-catalysed reaction of compounds of the formulas (II) and (III) as described in L. Churchatprasert, et al, J.Chem.Soc., Perkin I, 1779 (1992)

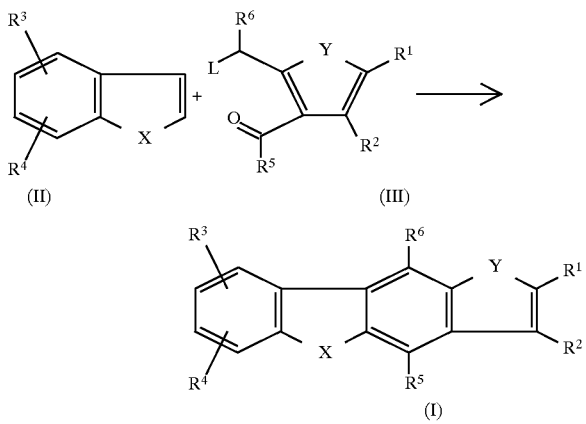

where L is a leaving group e.g. $OCOCH_3$, OMe, OEt, $N^+Me_3$, halo and $R^1$, $R^2$, $R^3$, $R^4$, $R^5$, $R^6$, X, Y as defined herein.

In addition compounds of the formula (I) with $R^2$=H and Y=NH may be prepared by the reaction of compounds (IV) and (V) under basic conditions at a temperature between $-20°$ C. and $+20°$ C. The reaction proceeds via an azide intermediate (VI) which is cyclised to compound (I) by heating in an appropriate solvent e.g. xylene.

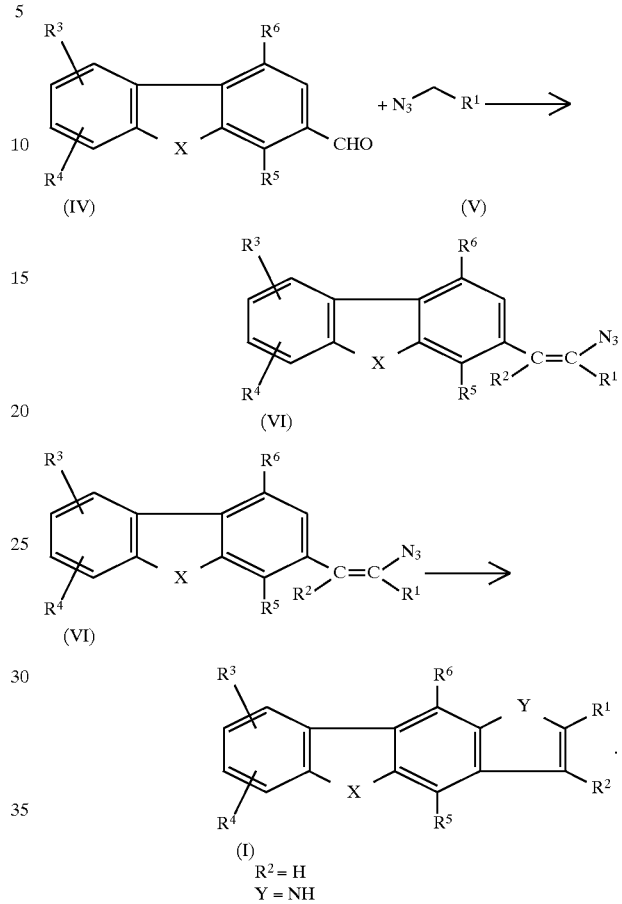

$R^1$, $R^3$, $R^4$, $R^5$, $R^6$, X as defined herein.

Compounds of the invention wherein $R^1$ is $COOR^8$ and $R^8$ is, for example, aralkyl can be converted to free acids wherein $R^8$ is H by reduction in the presence of $H_2$ and a Pd catalyst, or where $R^8$ is, for example, alkyl, by hydrolysis in the presence of an appropriate base e.g. caesium carbonate.

It is thereafter possible for the skilled man to synthesise other compounds, for example esters, amides, thionoesters, dithioesters, thiol esters, thioamides, and nitriles, and from the latter the imidate esters, from the acids by known procedures (see J. March, Advanced Organic Chemistry, 3rd Edition, Wiley-Interscience, New York, 1985).

A preferred method of preparing the esters ($R^1$=$COOR^8$) from the acids is by reaction of the acid with carbonyl diimidazole in, for example, tetrahydrofuran followed by addition of the alcohol and heating of the mixture at reflux. (H. A. Staab, Angew.Chem., Int.Ed.Engl., Vol. 1, (1962) 351–367.

Compounds of the invention produced as described herein can be converted to other compounds of the invention by electrophilic substitution at $R^5$ and/or $R^6$, to introduce, for example, $NO_2$, halogen, CHO and $COR^{13}$ wherein $R^{13}$ is as defined herein.

The compounds of the present invention are useful for the treatment of tumours. They may be employed in treating various forms of cancer of mammals including carcinomas, for instance of the stomach, pancreas, breast, uterus and colon; adenocarcinomas, for instance of the lung and colon;

sarcomas, for instance fibrosarcoma; leukaemias, for instance lymphocytic leukaemia and lymphomas, for instance myeloid lymphoma.

The invention thus further provides a method for the treatment of tumours in animals, including mammals, especially humans, which comprises the administration of a clinically useful amount of compound of formula (I) or a pharmaceutically acceptable salt or physiologically functional derivative in a pharmaceutically useful form, once or several times a day or in any other appropriate schedule, orally, rectally, parenterally, or applied topically.

In addition, there is provided as a further, or alternative, aspect of the invention, a compound of formula (I) or a pharmaceutically acceptable salt or physiologically functional derivative thereof for use in therapy, for example as an antitumour agent.

The amount of compound of formula (I) required to be effective against the aforementioned tumours will, of course, vary and is ultimately at the discretion of the medical or veterinary practitioner. The factors to be considered include the condition being treated, the route of administration, and nature of the formulation, the mammal's body weight, surface area, age and general condition, and the particular compound to be administered. A suitable effective antitumour dose is in the range of about 0.01 to about 100 mg/kg body weight, eg 0.1 to about 100 mg/kg body weight, preferably 1–30 mg/kg body weight. The total daily dose may be given as a single dose, multiple doses, e.g., two to six times per day or by intravenous infusion for selected duration. For example, for a 75 kg mammal, the dose range would be about 8 to 900 mg per day, and a typical dose could be about 50 mg per day. If discrete multiple doses are indicated treatment might typically be 15 mg of a compound of formula (I) given up to 4 times per day.

Whilst it is possible for the active compound to be administered alone, it is preferable to present the active compound in a pharmaceutical formulation. Formulations of the present invention, for medical use, comprise a compound of formula (I) or a salt thereof together with one or more pharmaceutically acceptable carriers and optionally other therapeutic ingredients. The carrier(s) should be pharmaceutically acceptable in the sense of being compatible with the other ingredients of the formulation and not deleterious to the recipient thereof.

The present invention, therefore, further provides a pharmaceutical formulation comprising a compound of formula (I) or a pharmaceutically acceptable salt or physiologically functional derivative thereof together with a pharmaceutically acceptable carrier thereof.

There is also provided a method for the preparation of a pharmaceutical formulation comprising bringing into association a compound of formula (I) or a pharmaceutically acceptable salt or physiologically functional derivative thereof, and a pharmaceutically acceptable carrier thereof.

Formulations according to the present invention include those suitable for oral, topical, rectal or parenteral (including subcutaneous, intramuscular and intravenous) administration. Preferred formulations are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a solution or suspension in an aqueous or non-aqueous liquid such as a syrup, an elixir, an emulsion or a draught.

A tablet may be made by compression or moulding, optionally with one or more accessory ingredients. Compressed tablets may be prepared by compressing in a suitable machine the active compound in a free-flowing form such as a powder or granules, optionally mixed with a binder, lubricant, inert diluent, surface active or dispersing agent. Moulded tablets may be made by moulding in a suitable machine a mixture of the powdered active compound with any suitable carrier.

A syrup may be made by adding the active compound to a concentrated, aqueous solution of a sugar, for example sucrose, to which may also be added any accessory ingredients. Such accessory ingredients(s) may include flavourings, an agent to retard crystallisation of the sugar or an agent to increase the solubility of any other ingredients, such as a polyhydric alcohol for example glycerol or sorbitol.

Formulations for rectal administration may be presented as a suppository with a conventional carrier such as cocoa butter.

Formulations suitable for parenteral administration conveniently comprise a sterile aqueous preparation of the active compound which is preferably isotonic with the blood of the recipient. Such formulations suitably comprise a solution of a pharmaceutically and pharmacologically acceptable acid addition salt of a compound of the formula (I) that is isotonic with the blood of the recipient.

Useful formulations also comprise concentrated solutions or solids containing the compound of formula (I) which upon dilution with an appropriate solvent give a solution for parenteral administration as above.

In addition to the aforementioned ingredients, the formulations of this invention may further include one or more accessory ingredient(s) selected from diluents, buffers, flavouring agents, binders, surface active agents, thickeners, lubricants, preservatives (including antioxidants) and the like.

In a further aspect the present invention provides the use of a compound of formula (I) or a pharmaceutically acceptable salt or physiologically functional derivative thereof for the manufacture of a medicament for the treatment of tumours.

The invention will now be illustrated by the following non-limiting Examples:

All temperatures are in degrees Celsius (°C.)

IR spectra were recorded on a Perkin-Elmer 257 grating spectrophotometer or a Bruker FS66 spectrophotometer.

U.V. spectra were measured in ethanol on a Unicam SP800 spectrophotometer.

1H NMR spectra were obtained on a Bruker WM 360-NMR spectrophotometer or a Bruker AMX-360 NMR spectrophotometer at 360 MHz, or on a Bruker AC200 spectrophotometer at 200 MHz. J values are given in Hz.

Mass spectra were obtained on Varian CH5D(EI), Kratos Concept (EI) or Kratos Ms50(FAB) instruments.

Preparation of Intermediates 3,4-Dimethylpyrrolo[3,2-b]carbazole-2-carboxylic acid was prepared according to the method of L. Churchatprasert et al. J. Chem. Soc., Perkin Trans. I, 1779 (1992).

4-Methyl-1H-[1]benzothieno[2,3-f]indole-2-carboxylic acid was prepared via the corresponding ethyl ester as described below:

Ethyl 4-methyl-1H-[1]benzothieno[2,3-f]indole-2-carboxylate

Sodium (1.6 g, 70 mmol) was dissolved in dry ethanol (175 ml) and the solution cooled to 0° C. A mixture of 4-methyldibenzothiophene-3-carboxaldehyde (prepared according to the method of E. Campaigne et al., J. Heterocyclic Chem., 6, 553 (1969)) (4.0 g, 18 mmol) and ethyl 2-azidoacetate (11.7 g, 91 mmol) in THF (25 ml) was added dropwise to the sodium ethoxide solution. The reaction mixture was stirred at 0° C. for 3 h giving a yellow precipitate. The yellow precipitate was collected by filtration and dissolved in ether, and the resulting solution was filtered and concentrated in vacuo to give an unstable yellow solid (2.86 g). This solid was added to xylene (150 ml) at reflux, and heating continued for 5 min. The reaction mixture was cooled and concentrated in vacuo. The material was triturated with ethyl acetate/petrol to give the product as a yellow solid (1.38 g, 25% from the aldehyde) with m.p. 219°–220° C. (Found: C, 69.63; H, 4.81; N, 4.31. $C_{18}H_{15}NO_2S$ requires: C, 69.88; H, 4.89; N, 4.53%); δH [$^2H_6$]-DMSO 12.08 (1H, s, 1-NH), 8.25–8.38 (1H, m, 9-H), 8.19 (1H, s, 10-H), 7.89–8.00 (1H, m, 6-H), 7.42–7.58 (2H, m, 7-H, 8-H), 7.48 (1H, s, 3-H), 4.39 (2H, q, J 6.5, OC$\underline{H}_2$CH$_3$), 2.74 (3H, s, 4-CH$_3$), 1.43 (3H, t, J 7, OCH$_2$C$\underline{H}_3$); m/z (%) 309 (78, M$^+$), 263) (100), 235 (35); $v_{max}$ (KBr disc)/cm$^{-1}$ 3325, 1686, 1215.

4-Methyl-1H-[1]benzothieno[2,3-f]indole-2-carboxylic acid

Ethyl 4-methyl-1H-[1]benzothieno[2,3-f]indole-2-carboxylate (1.0 g, 3.2 mmol) was suspended in a mixture of methanol (110 ml) and water (30 ml). Casium carbonate (10 g) was added and the mixture was heated at reflux under nitrogen for 2 h. The solution was allowed to cool to room temperature, and the methanol was removed in vacuo. The solution was acidified with 0.1 Molar Hydrochloric acid and the resulting yellow precipitate was collected by fitration and washed with water. The wet precipitate was dissolved in acetone and the solvent removed in vacuo to give the product as a yellow solid with m.p. 271°–272° C.; δH [$^2H_6$]-DMSO 11.88 (1H, s, 1-NH), 8.29 (1H, dd, J 6, 3, 9H), 8.18 (1H, s, 10-H), 7.89–7.99 (1H, m, 6-H), 7.44–7.54 (2H, m, 7-H, 8-H), 7.35 (1H, d, J 2, 3-H), 2.72 (3H, s, 4-CH$_3$); m/z (%) 281 (90, M$^+$), 263 (100), 235 (69).

Ethyl 3-bromo-4-methyl-1H-[1]benzothieno[2,3-f]indole-2-carboxaylate

Ethyl 4-methyl-1H-[1]benzothieno[2,3-f]indole-2-carboxylate (0.500 g, 1.6 mmol) was dissolved in dry pyridine (20 ml). The solution was cooled to 0° C. and a solution of pyridinium bromide perbromate (0.540 g, 1.7 mmol) in pyridine (10 ml) was added dropwise. The reaction was stirred at 0° C. for 2 h and then at room temperature for 48 h. The solvent was removed in vacuo, and the residue was dissolved in ethyl acetate. This solution was washed with water (×2), dried (MgSO$_4$) and concentrated in vacuo Recrystallisation from toluene gave the product as a yellow solid (0.410 g, 65%) with m.p. 215°–216° C. (decomp.) (Found: C, 55.25; H, 3.40; N, 3.56. $C_{18}H_{14}BrNO_2S$ requires: C, 55.68; H, 3.63; N, 3.61%); δH [$^2H_6$]-DMSO 12.42 (1H, s, 1-NH), 8.24–8.32 (1H, m, 9-H), 8.21 (1H, s, 10-H), 7.91–8.00 (1H, m, 6-H), 7.44–7.55 (2H, m, 7-H, 8-H), 4.43 (2H, q, J 7, OC$\underline{H}_2$CH$_3$), 3.04 (3H, s, 4-CH$_3$), 1.43 (3H, t, J 7, OCH$_2$C$\underline{H}_3$); m/z (%) 389 and 387 (46, 44, M$^+$), 343 and 341 (74, 72), 234 (100); $v_{max}$ (KBr disc)/cm$^{-1}$ 3315, 1660, 1308.

2-Hydroxymethyl-4-methyl-1H-[1]benzothieno[2,3-f]indole

Ethyl 4-methyl-1H-[1]benzothieno[2,3-f]indole-2-carboxylate (0.155 g, 0.5 mmol) was suspended in dichloromethane (2 ml) and cooled to −78° C. Diisobutylaluminium hydride solution (1.0 molar solution in hexane, 1.25 ml) was added and the mixture was stirred at −78° C., for 1 h, and then allowed to warm to room temperature. Stirring was continued for 2 h. Methanol (0.2 ml) and saturated aqueous potassium sodium tartrate solution (4 ml) were added, the phases were separated and the aqueous phase was extracted with dichloromethane. The combined organic phases were dried (MgSO$_4$), and the solvent removed in vacuo. The residue was purified by column chromatography (gradient elution with ethyl acetate/petrol) to give the product as a beige solid (0.017 g, 13%) with m.p. 154°–155° C. (Found: C, 72.10; H, 4.94; N, 5.15. $C_{16}H_{13}NOS$ requires: C, 71.88; H, 4.90; N, 5.24%); δH [$^2H_6$]-DMSO 11.22 (1H, s, 1-NH), 8.24–8.41 (1H, m, 9-H), 8.10 (1H, s, 10-H), 7.88–7.98 (1H, m, 6-H), 7.38–7.50 (2H, m, 7-H, 8-H), 6.48 (1H, br s, 3-H), 5.34 (1H, t, J 5.5, OH), 4.69 (2H, d, J 5.5, 2-CH$_2$), 2.65 (3H, s, 4-CH$_3$); m/z (%) 267 (100, M$^+$), 251 (90), 236 (23); $v_{max}$ (KBr disc)/cm$^{-1}$ 3698, 1009, 758.

General Procedure for Preparation of Esters

Pyrrolo[3,2-b]carbazole-2-carboxylic acid (1.0 mmol) (or 4-methyl-1H-benzothieno[2,3-f]indole-2-carboxylic acid where appropriate) and carbonyl diimidazole (1.1 mmol) were dissolved in freshly distilled tetrahydrofuran under a nitrogen atmosphere. The resulting suspension was stirred at room temperature for at least one hour, and complete conversion of the acid to the imidazolide intermediate was verified by TLC. The alcohol or phenol (1.5–2.0 mmol, i.e. an excess) was added in one portion, together with the catalytic NaOMe (0.1 eq) where necessary, and the resulting mixture was heated at reflux until TLC showed complete consumption of the imidazolide intermediate. The product was obtained by column chromatography on silica, and/or recrystallisation.

A: Substituted Alkyl Esters

EXAMPLE 1

[(2-Dimethylamino)ethyl]3,4-dimethylpyrrolo[3,2-b]carbazole-2-carboxylate was obtained from the reaction of the imidazolide intermediate with (2-dimethylamino)ethanol. Chromatography (eluting with 10% methanol/90% DCM) gave a yellow solid (0.350 g, 99%). Recrystallisation of a portion from DCM gave yellow crystals with m.p. 174.0°–175.7° C. (decomp.) (Found: C, 70.14; H, 6.48; N, 11.60%. $C_{21}H_{23}N_3O_2.0.15CH_2Cl_2$ requires: C, 70.29; H, 6.45; N, 11.55%); δH [$^2H_6$]-DMSO 11.18 (1H, s, 1-NH), 10.60 (1H, s, 5-NH), 8.07 (1H, d, J 8, 9-H), 7.89 (1H, s, 10-H), 7.30–7.43 (2H, m, 6-H, 7-H), 7.09 (1H, ddd, J 8, 6, 2.5, 8-H), 4.41 (2H, t, J 6, OCH$_2$), 2.91 (6H, s, 3-CH$_3$ and 4-CH$_3$), 2.69 (2H, t, J 6, NCH$_2$), 2.25 (6H, s, N(CH$_3$)$_2$); m/z (%) 350 (46, M+1$^+$), 261 (68), 133 (100); $v_{max}$ (KBr disc)/cm$^{-1}$ 3377, 1661, 1238.

EXAMPLE 2

(2-Methylsulphonylethyl) 3,4-dimethylpyrrolo[3,2-b]carbazole-2-carboxylate was obtained from the reaction of the imidazolide intermediate with 2-methylsulphonylethanol. Chromatography (gradient elution with ethyl acetate/petrol, 30%–100%) followed by recrystallisation from acetone gave fine yellow crystals (0.222 g, 57%) with m.p. 255°–257° C. (decomp.) (Found: C, 62.23; H, 5.25; N, 7.08. $C_{20}H_{20}N_2O_4S$ requires: C, 62.48;

H, 5.24; N, 7.29%); δH [$^2$H$_6$]-DMSO 11.19 (1H, s, 1-NH), 10.60 (1H, s, 5-NH), 8.09 (1H, d, J 7.5, 9-H), 7.89 (1H, s, 10-H), 7.32–7.45 (2H, m, 6-H, 7-H), 7.09 (1H, ddd, J 7.5, 5.5, 3, 8-H), 4.69 (2H, t, J 5.5, OCH$_2$), 3.69 (2H, t, J 5.5, SO$_2$CH$_2$), 3.12 (3H, s, SO$_2$CH$_3$), 2.93 (6H, s, 3-CH$_3$ and 4-CH$_3$); m/z (%) 384 (17, M$^+$), 260 (13), 59 (100); ν$_{max}$ (KBr disc)/cm$^{-1}$ 3387, 1661, 1234.

EXAMPLE 3

(2-Methylsulphinylethyl) 3,4-dimethylpyrrolo[3,2-b]carbazole-2-carboxylate was obtained from the reaction of the imidazolide intermediate with 2-methylsulphinylethanol. Due to insolubility the material could not be purified by chromatography. The residue from the reaction (after removal of solvent) was washed with methanol, and the resulting yellow solid was recrystallised from 2-methoxyethanol and water to give orange needles (0.205 g, 56%) with m.p. 263°–265° C. (decomp.) (Found: C, 65.25; H, 5.47; N, 7.39. C$_{20}$H$_{20}$N$_2$O$_3$S requires: C, 65.20; H, 5.47; N, 7.60%); δH [$^2$H$_6$]-DMSO 11.22 (1H, s, 1-NH), 10.60 (1H, s, 5-NH), 8.07 (1H, d, J 8, 9-H), 7.89 (1H, s, 10-H), 7.30–7.45 (2H, m, 6-H, 7-H), 7.08 (1H, ddd, J 8, 5.5, 2.5, 8-H), 4.53–4.80 (2H, m, OCH$_2$), 3.05–3.49 (2H, m, SOCH$_2$), 2.91 (6H, s, 3-CH$_3$ and 4-CH$_3$), 2.69 (3H, s, SOCH$_3$); m/z (%) 368 (20, M$^+$), 352 (68), 291 (34), 260 (62), 57 (92), 43 (100); ν$_{max}$ (KBr disc)/cm$^{-1}$ 3371, 1657, 1234.

EXAMPLE 4

(1,3-Dibenzyloxypropyl-2) 3,4-dimethylpyrrolo[3,2-b]carbazole-2-carboxylate was obtained from the reaction of the imidazolide intermediate with 1,3-dibenzyloxy-2-propanol on 1.5 times the usual scale and using catalytic NaOMe. Chromatography (gradient elution with ethyl acetate/petrol 20%–40%) gave the product (0.776 g, 97%). Recrystallisation of a portion from ethyl acetate-ether-petrol gave yellow crystals with m.p. 124.5°–126° C. (decomp.) (Found: C, 76.35; H, 6.07; N, 5.12. C$_{34}$H$_{32}$N$_2$O$_4$ requires: C, 76.67; H, 6.06; N, 5.26%); δH [$^2$H$_6$]-DMSO 11.18 (1H, s, 1-NH), 10.60 (1H, s, 5-NH), 8.06 (1H, d, J 7.5, 9-H), 7.88 (1H, s, 10-H), 7.22–7.42 (12H, m, 2×PhH$_5$, 6-H, 7-H), 7.07 (1H, ddd, J 8, 6.5, 1.5, 8-H), 5.44 (1H, quintet, J 5, 2'-H), 4.60 and 4.53 (2×2H, 2×d, J 12, 2×PhCH$_2$O), 3.77 (4H, d, J 5.5, OCH(CH$_2$)$_2$), 2.91 and 2.89 (2×3H, 2×s, 3-CH$_3$ and 4-CH$_3$); m/z (%) 532 (50, M$^+$), 260 (65), 91 (100); ν$_{max}$ (KBr disc)/cm$^{-1}$ 3358, 1681, 1234.

EXAMPLE 5

(1-Benzyloxy-3-hydroxypropyl-2) 3,4-dimethylpyrrolo[3,2-b]carbazole-2-carboxylate and (1,3-Dihydroxypropyl-2) 3,4-dimethylpyrrolo[3,2-b]carbazole-2-carboxylate These compounds were obtained by the reaction of (1,3-dibenzyloxypropyl-2) 3,4-dimethylpyrrolo[3,2-b]carbazole-2-carboxylate with cyclohexene in the presence of 10% Pd-C (100 mg per mmol) in refluxing EtOAc (transfer hydrogenation). A large excess of cyclohexene was used, added once or twice daily over 10–14 days. When the reaction had progressed to the desired extent (as judged by TLC), the reaction mixture was filtered through Hyflo, and the resulting filtrate and washings were concentrated in vacuo. Chromatography (gradient elution with ethyl acetate/petrol, 50%–100%, then 10% methanol/ethyl acetate) gave three products (the ratio depending on the length of time of the reaction).

The least polar material was recovered dibenzyloxy compound, identical to the starting material described in Example 4.

The second compound eluted from the column was (1-benzyloxy-3-hydroxypropyl-2) 3,4-dimethylpyrrolo[3,2-b]carbazole-2-carboxylate (Example 5a), obtained as yellow crystals which did not melt up to 340° C. (but discoloured gradually above 270° C.) (Found: C, 73.30; H, 6.04; N, 6.15. C$_{27}$H$_{26}$N$_2$O$_4$ requires: C, 73.29; H, 5.92; N, 6.33%); δH [$^2$H$_6$]-DMSO 11.13 (1H, s, 1-NH), 10.60 (1H, s, 5-NH), 8.08 (1H, d, J 7.5, 9-H), 7.90 (1H, s, 10-H), 7.26–7.44 (7H, m, PhH$_5$, 6-H, 7-H), 7.08 (1H, ddd, J 8, 6, 2, 8-H), 5.27 (1H, quintet, J 5, 2'-H), 4.94 (1H, br t, J 5.5, 3'-OH), 4.59 and 4.51 (2×1H, 2×d, J 12, PhCH$_2$O), 3.69–3.79 (4H, m, 1'-H$_2$, 3'-H$_2$), 2.90 and 2.89 (2×3H, 2×s, 3-CH$_3$ and 4-CH$_3$); m/z (%) 442 (2, M$^+$), 260 (60), 91 (90), 43 (100); ν$_{max}$ (KBr disc)/cm$^{-1}$ 3348, 1670, 1238.

The final compound eluted from the column was (1,3-dihydroxypropyl-2) 3,4-dimethylpyrrolo[3,2-b]carbazole-2-carboxylate (Example 5b), obtained as a yellow solid with m.p. 225°–227° C. (decomp.) (Found: C, 66.98; H, 5.83; N, 7.54. C$_{20}$H$_{20}$N$_2$O$_4$.0.4H$_2$O requires: C, 66.80; H, 5.83; N, 7.79%); δH [$^2$H$_6$]-DMSO 11.06 (1H, s, 1-NH), 10.60 (1H, s, 5-NH), 8.06 (1H, d, J 7.5, 9-H), 7.87 (1H, s, 10-H), 7.30–7.43 (2H, m, 6-H, 7-H), 7.07 (1H, ddd, J 8, 6.5, 1.5, 8-H), 5.00 (1H, quintet, J 5, 2'-H), 4.83 (2H, br t, J 5.5, 1'-OH, 3'-OH), 3.68 (4H, t, J 5, 1'-H$_2$, 3'-H$_2$), 2.90 and 2.89 (2×3H, 2×s, 3-CH$_3$ and 4-CH$_3$); m/z (%) 352 (54, M$^+$), 260 (100), 232 (37); ν$_{max}$ (KBr disc)/cm$^{-1}$ 3373, 1657, 1236.

EXAMPLE 6

(2-Amino-2-methylpropyl-1) 3,4-dimethylpyrrolo[3,2-b]carbazole-2-carboxylate was obtained from the reaction of the imidazolide intermediate with 2-amino-2-methylpropanol, but at room temperature (not reflux), for 48 hours. Removal of solvent followed by recrystallisation from DMF/water gave a yellow solid (0.200 g, 57%) with m.p. 218°–220° C. (decomp.) (Found: C, 70.87; H, 6.43; N, 11.86. C$_{21}$H$_{23}$N$_3$O$_2$.0.3H$_2$O requires: C, 71.08; H, 6.70; N, 11.85%); δH [$^2$H$_6$]-DMSO 11.15 (1H, s, 1-NH), 10.60 (1H, s, 5-NH), 8.08 (1H, d, J 8, 9-H), 7.89 (1H, s, 10-H), 7.30–7.47 (2H, m, 6-H, 7-H), 7.09 (1H, ddd, J 8, 6, 3, 8-H), 4.03 (2H, s, 1'-H$_2$), 2.92 and 2.91 (2×3H, 2×s, 3-CH$_3$ and 4-CH$_3$), 1.75 (<2H, br s, ex NH$_2$), 1.16 (6H, s, 2'-CH$_3$, 3'-H$_3$); m/z (%) 349 (53, M$^+$), 278 (78), 260 (100), 232 (56), 58 (48); ν$_{max}$ (KBr disc)/cm$^{-1}$ 3350, 1676, 1236.

EXAMPLE 7

(4-Nitrophenylmethyl)2-(3,4-dimethylpyrrolo[3,2-b]carbazole-2-carboxy)acetate was obtained from the standard reaction of the imidazolide intermediate with (4-nitrophenylmethyl)-2-hydroxyacetate. Due to insolubility the material could not be purified by chromatography. The residue from the reaction (after removal of solvent) was redissolved in TBF and precipitated with petrol to give the product as an orange powder (0.350 g, 74%). Recrystallisation of a portion from THF-petrol gave orange microcrystals with m.p. 248°–249° C. (decomp.) (Found: C, 66.01; H, 4.38; N, 8.68. C$_{26}$H$_{21}$N$_3$O$_6$ requires: C, 66.24; H, 4.49; N, 8.91%); δH [$^2$H$_6$]-DMSO 11.39 (1H, s, 1-NH), 10.64 (1H, s, 5-NH), 8.28 (2H, d, J 9, 3'-H, 5'-H), 8.09 (1H, d, J 8, 9-H), 7.90 (1H, s, 10-H), 7.70 (2H, d, J 9, 2'-H, 6'-H), 7.32–7.45 (2H, m, 6-H, 7-H), 7.09 (1-H, ddd, J 8, 6, 3, 8-H), 5.42 and 5.10 (2×2H, 2×s, OCH$_2$Ar and OCOCH$_2$CO), 2.91 (6H, s, 3-CH$_3$ and 4-CH$_3$); m/z (%) 471 (84, M$^+$), 381 (100), 260 (87); ν$_{max}$ (KBr disc)/cm$^{-1}$ 3427, 3362, 1697, 1672, 1181.

EXAMPLE 8

2-(3,4-Dimethylpyrrolo[3,2-b]carbazole-2-carboxyy) acetic acid was obtained by the catalytic hydrogenation of (4-nitrophenylmethyl)-2-(3,4-dimethylpyrrolo[3,2-b] carbazole-2-carboxy)acetate (0.236 g, 0.5 mmol) in THF (10 ml) using 10% Pd-C (11% by mass) for 22 h at atmospheric pressure. The reaction mixture was filtered through Hyflo to remove the catalyst, washing with excess THF, and the combined filtrate and washings were concentrated to a yellow solid. Chromatography (gradient elution with methanol/ethyl acetate, 10%–60%) followed by recrystallisation from acetic acid-petrol gave the product as a yellow powder (0.104 g, 62%), which did not melt up to 330° C. (but discoloured gradually above 250° C.); δH [$^2$H$_6$]-DMSO 11.30 (1H, s, 1-NH), 10.60 (1H, s, 5-NH), 8.08 (1H, d, J 9, 9-H), 7.89 (1H, s, 10-H), 7.32–7.45 (2H, m, 6-H, 7-H), 7.09 (1H, ddd, J 9, 6.5, 2.5, 8-H), 4.29 (2H, s, OC$\underline{H}_2$CO$_2$), 2.90 (6H, s, 3-CH$_3$ and 4-CH$_3$); m/z (%) 336 (3, M$^+$), 318 (20), 260 (20), 234 (45), 59 (100); ν$_{max}$ (KBr disc)/cm$^{-1}$ 3348, 1703, 1674, 1232; (Found: M$^+$ 336.1116, C$_{19}$H$_{16}$N$_2$O$_4$ requires 336.1110).

B: Cycloalkyl and Substituted Cycloalkyl Esters

EXAMPLE 9

Cyclohexyl 3,4-dimethylpyrrolo[3,2-b]carbazole-2-carboxylate was obtained from the reaction of the imidazolide intermediate with cyclohexanol with the addition of catalytic sodium methoxide. Chromatography (gradient elution with diethyl ether/petrol, 20%–40%) followed by recrystallisation from ethyl acetate gave fine yellow crystals (0.202 g, 56%) with m.p. 267°–269° C. (decomp.) (Found: C, 76.36; H, 6.67; N, 7.55. C$_{23}$H$_{24}$N$_2$O$_2$ requires: C, 76.64; H, 6.71; N, 7.77%); δH [$^2$H$_6$]-DMSO 11.10 (1H, s, 1-NH), 10.60 (1H, s, 5-NH), 8.07 (1H, d, J 8, 9-H), 7.89 (1H, s, 10-H), 7.30–7.43 (2H, m, 6-H, 7-H), 7.09 (1H, ddd, J 8, 6, 3, 8-H), 4.95–5.09 (1H, m, 1'-H), 2.90 (6H, s, 3-CH$_3$ and 4-CH$_3$), 1.35–2.03 (10H, m, 2'-H$_2$, 3'-H$_2$, 4'-H$_2$, 5'-H$_2$, 6'-H$_2$); m/z (%) 360 (57, M$^+$), 278 (28), 260 (100), 177 (68), 57 (83); ν$_{max}$ (KBr disc)/cm$^{-1}$ 3335, 1668, 1236.

EXAMPLE 10

Cyclohexylmethyl 3,4-dimethylpyrrolo[3,2-b]carbazole-2-carboxylate was obtained from the reaction of the imidazolide intermediate with cyclohexylmethanol. Chromatography (gradient elution with ethyl acetate/petrol, 10%–30%) gave a yellow solid (0.290 g, 79%). Recrystallisation of a portion from ethyl acetate gave a yellow crystalline solid with m.p. 244°–245° C. (decomp.) (Found: C, 76.62; H, 6.92; N, 7.32. C$_{24}$H$_{26}$N$_2$O$_2$ requires: C, 76.98; H, 7.00; N, 7.48%); δH [$^2$H$_6$]-DMSO 11.13 (1H, s, 1-NH), 10.61 (1H, s, 5-NH), 8.07 (1H, d, J 7.5, 9H), 7.89 (1H, s, 10-H), 7.30–7.45 (2H, m, 6-H, 7-H), 7.09 (1H, ddd, J 8, 6, 3, 8-H), 4.16 (2H, d, J 6, OCH$_2$), 2.90 (6H, s, 3-CH$_3$ and 4-CH$_3$), 1.60–1.92 (6H, m) and 1.00–1.40 (5H, m) (1'-H, 2'-H$_2$, 3'-H$_2$, 4'-H$_2$, 5'-H$_2$, 6'-H$_2$); m/z (%) 374 (53, M$^+$), 260 (100), 231 (82); ν$_{max}$ (KBr disc)/cm$^{-1}$ 3332, 1672, 1309, 1238.

EXAMPLE 11

Cyclopentyl 3,4-dimethylpyrrolo[3,2-b]carbazole-2-carboxylate was obtained from the reaction of the imidazolide intermediate with cyclopentanol with the addition of catalytic sodium methoxide. Chromatography (gradient elution with diethyl ether/petrol, 10%–30%) gave an orange-yellow solid (0.184 g, 53%). Recrystallisation of a portion from diethyl ether/petrol gave yellow crystals with m.p. 267°–269° C. (decomp.) (Found: C, 75.74; H, 6.63; N, 7.59. C$_{22}$H$_{22}$N$_2$O$_2$.0.2Et$_2$O requires: C, 75.81; H, 6.70; N, 7.75%); δH [$^2$H$_6$]-DMSO 11.09 (1H, s, 1-NH), 10.60 (1H, s, 5-NH), 8.08 (1H, d, J 8, 9-H), 7.89 (1H, s, 10-H), 7.29–7.47 (2H, m, 6-H, 7-H), 7.09 (1H, ddd, J 8, 6, 2, 8-H), 5.33–5.44 (1H, m, 1'-H), 3.39 (quart, J 7, ether), 2.90 and 2.89 (2×3H, 2×s, 3-CH$_3$ and 4-CH$_3$), 1.58–2.10 (8H, m, 2'-H$_2$, 3'-H$_2$, 4'-H$_2$, 5'-H$_2$), 1.10 (t, J 7, ether); m/z (%) 346 (55, M$^+$), 278 (15), 260 (89), 231 (31), 43 (100); ν$_{max}$ (KBr disc)/cm$^{-1}$ 3329, 1670, 1238.

EXAMPLE 12

Cyclooctyl 3,4-dimethylpyrrolo[3,2-b]carbazole-2-carboxylate was obtained from the reaction of the imidazolide intermediate with cyclooctanol with the addition of catalytic sodium methoxide. Chromatography (gradient elution with ethyl acetate/petrol, 10%–30%) gave a yellow solid (0.274 g), which still contained excess cyclooctanol. Recrystallisation of a portion from ethyl acetate/petrol gave orange crystals with m.p. 235°–236° C. (decomp.) (Found: C, 77.05; H, 7.32; N, 7.07. C$_{25}$H$_{28}$N$_2$O$_2$ requires: C, 77.29; H, 7.26; N, 7.21%); δH [$^2$H$_6$]-DMSO 11.09 (1H, s, 1-NH), 10.59 (1H, s, 5-NH), 8.07 (1H, d, J 7.5, 9-H), 7.89 (1H, s, 10-H), 7.30–7.47 (2H, m, 6-H, 7-H), 7.09 (1H, ddd, J 7.5, 6, 3, 8-H), 5.19 (1H, quintet, J 6, 1'-H), 2.90 and 2.89 (2×3H, 2×s, 3-CH$_3$ and 4-CH$_3$), 1.50–2.05 (14H, m, 2'-H$_2$, 3'-H$_2$, 4'-H$_2$, 5'-H$_2$, 6'-H$_2$, 7'-H$_2$, 8'-H$_2$); m/z (%) 388 (70, M$^+$), 278 (87), 260 (100), 231 (70); ν$_{max}$ (KBr disc)/cm$^{-1}$ 3352, 1662, 1238.

EXAMPLE 13

3,5-Di(tert-butyldiphenylsilyloxy)cyclohexyl 3,4-dimethylpyrrolo[3,2-b]carbazole-2-carboxylate was obtained from the reaction of the imidazolide intermediate with 3,5-di(tert-butyldiphenylsilyloxy)-cyclohexanol (prepared according to the method of M. Carda, J. Van der Eyken, M. Vanderwalle, Tetrahedron Asymmetry, 1990, 1, 17–20) with the addition of catalytic sodium methoxide. Chromatography (gradient elution with toluene/petrol, 50%–100% then 10% ethyl acetate/toluene) gave a yellow solid (0.581 g, 69%). Recrystallisation of a portion from diethyl ether/petrol gave a pale yellow powder with m.p. 203°–205° C. (decomp.) (Found: C, 76.04; H, 7.14; N, 3.19. C$_{55}$H$_{60}$N$_2$O$_4$Si$_2$ requires: C, 76.00; H, 6.96; N, 3.22%); δH [$^2$H$_6$]-DMSO 11.10 (1H, s, 1-NH), 10.60 (1H, s, 5-NH), 8.09 (1H, d, J 8, 9-H), 7.88 (1H, s, 10-H), 7.32–7.49 (22H, m, 6-H, 7-H, 20×PhH), 7.08 (1H, ddd, J 7.5, 6, 2.5, 8-H), 4.58–4.73 (1H, m, 1'-H), 3.55–3.70 (2H, m, 3'-H, 5'-H), 2.90 and 2.87 (2×3H, 2×s, 3-CH$_3$ and 4-CH$_3$), 2.15–2.29 (2H, m, 2'-Heq, 6'-Heq), 1.92–2.04 (1H, m, 4'-Heq), 1.40–1.70 (3H, m, 2'-Hax, 4'-Hax, 6'-Hax), 0.98 (18H, s, 2×C(CH$_3$)$_3$); m/z (%) 869 (5, M+1$^+$), 291 (15), 261 (35), 197 (40), 135 (100); ν$_{max}$ (KBr disc)/cm$^{-1}$ 1232, 1113, 1076, 702.

EXAMPLE 14

3,5-Dihydroxycyclohexyl 3,4-dimethylpyrrolo[3,2-b]carbazole-2-carboxylate 3,5-Di(tert-butyldiphenylsilyloxy)cyclohexyl 3,4-dimethylpyrrolo[3,2-b]carbazole-2-carboxylate (0.435 g, 0.50 mmol) was dissolved in freshly distilled THF (5 ml) under a nitrogen atmosphere and treated with a solution of tetra-n-butyl ammonium fluoride in THF (1.1M, 1.8 ml, 1.98 mmol) and further THF (5 ml). This mixture was heated to 60° C. for 2.5 hours, by which time TLC showed complete disappearance of the starting material. The reaction mixture was partitioned between ether and water, and the organic layer was washed with brine. The aqueous layer was further extracted with DCM. Both sets of organic extracts were dried (MgSO$_4$), combined and concentrated in vacuo to a yellow solid. Chromatography (gradient elution with methanol/DCM, 10%–15%) gave a yellow oil which was crystallised from ethanol/water to give a yellow powder (0.138 g, 67%) with m.p. 273°–275° C. (decomp.) (Found: C, 67.33; H, 6.24; N, 6.62. C$_{23}$H$_{24}$N$_2$O$_4$H$_2$O requires: C, 67.30; H, 6.38; N, 6.82%); δH [$^2$H$_6$]-DMSO 11.04 (1H, s, 1-NH), 10.61 (1H, s, 5-NH), 8.09 (1H, d, J 8, 9-H), 7.89 (1H, s, 10-H), 7.31–7.47 (2H, m, 6-H, 7-H), 7.09 (1H, ddd, J 8, 6, 3, 8-H), 4.80–5.00 (1H, m 1'-H), 4.80 (2H, d, J 5, 3'-OH, 5'-OH), 3.47–3.69 (2H, m, 3'-H, 5'-H), 2.92 and 2.90 (2×3H, 2×s, 3-CH$_3$ and 4-CH$_3$), 2.19–2.34 (2H, m, 2'-Heq, 6'-Heq), 2.04–2.19 (1H, m, 4'-Heq), 1.06–1.47 (3H, m, 2'-Hax, 4'-Hax, 6'-Hax); m/z (%) 392 (73, M$^+$), 278 (37), 260 (100), 232 (64); ν$_{max}$ (KBr disc)/cm$^{-1}$ 3344, 1664, 1308, 1236.

EXAMPLE 15 cis-4-tert-Butyldiphenylsilyloxycyclohexyl 3,4-dimethylpyrrolo[3,2-b]carbazole-2-carboxylate was obtained from the reaction of the imidazolide intermediate with cis-4-(tert-butyldiphenylsilyloxy) cyclohexanol (prepared as a mixture with its trans isomer by the reaction of 1,4-cyclohexanediol with tert-butyldiphenylsilyl chloride and imidazole in DMF at room temperature, followed by separation by chromatography) on a 1.5 mmol scale with the addition of catalytic sodium methoxide. Chromatography (gradient elution with ethyl acetate/petrol, 10%–30%) gave a yellow solid (0.571 g, 62%). Recrystallisation of a portion from diethyl ether/petrol gave a yellow solid with m.p. 187°–189° C. (decomp.) (Found: C, 75.91; H, 6.94; N, 4.46. C$_{39}$H$_{42}$N$_2$O$_3$Si requires: C, 76.18; H, 6.88; N, 4.56%); δH [$^2$H$_6$]-DMSO 11.15 (1H, s, 1-NH), 10.61 (1H, s, 5-NH), 8.09 (1H, d, J 8, 9-H), 7.91 (1H, s, 10-H), 7.62–7.70 (4H, m, 2×2"-H, 2×6"-H), 7.31–7.53 (8H, m, 6-H, 7-H, 2×3"-H, 2×4"-H, 2×5"-H), 7.09 (1H, ddd, J 8.5, 6, 2, 8-H), 4.94–5.09 (1H, m, 1'-H), 3.85–3.99 (1H, m, 4'-H), 2.93 and 2.92 (2×3H, 2×s, 3-CH$_3$ and 4-CH$_3$), 1.50–2.10 (8H, m, 2'-H$_2$, 3'-H$_2$, 5'-H$_2$, 6'-H$_2$), 1.09 (9H, s, C(CH$_3$)$_3$); m/z (%) 614 (71, M$^+$), 278 (31), 260 (100), 232 (47), 199 (84); ν$_{max}$ (KBr disc)/cm$^{-1}$ 1664, 1234, 702.

EXAMPLE 16 cis-4-Hydroxycyclohexyl 3,4-dimethylpyrrolo[3,2-b]carbazole-2-carboxylate cis4-tert-Butyldiphenylsilyloxycyclohexyl 3,4-dimethylpyrrolo[3,2-b]carbazole-2-carboxylate (0.431 g, 0.70 mmol) was dissolved in freshly distilled THF (8 ml) under a nitrogen atmosphere and treated with a solution of tetra-n-butyl ammonium fluoride in THF (1.0M, 2.1 ml, 2.1 mmol). This mixture was heated to 60° C. for 1 hour, by which time TLC showed complete disappearance of the starting material. The reaction mixture was partitioned between ethyl acetate and water, and the organic layer was washed with brine. The aqueous layer was further extracted with ethyl acetate. The organic extracts were combined, dried (MgSO$_4$), and concentrated in vacuo to a yellow solid. Chromatography (gradient elution with ethyl acetate/petrol, 50%–100% followed by 5% methanol/ethyl acetate, then a second column using a gradient elution with ethyl acetate/petrol, 25%–100%) gave a yellow solid which was crystallised from ethyl acetate to give a yellow powder (0.184 g, 67%) with m.p. 258°–259° C. (decomp.) (Found: C, 70.88; H, 6.39; N, 6.93. C$_{23}$H$_{24}$N$_2$O$_3$.0.8H$_2$O requires: C, 70.67; H, 6.60; N, 7.17%); δH [$^2$H$_6$]-DMSO 11.11 (1H, s, 1-NH), 10.60 (1H, s, 5-NH), 8.06 (1H, d, J 8, 9-H), 7.89 (1H, s, 10-H), 7.30–7.45 (2H, m, 6-H, 7-H), 7.09 (1H, ddd, J 8, 6, 2.5, 8-H), 5.03–5.12 (1H, m, 1'-H), 4.59 (1H, d, J 4.5, 4'-OH), 3.55–3.70 (1H, m, 4'0 -H), 2.91 (6H, s, 3-CH$_3$ and 4-CH$_3$), 1.60–2.05 (8H, m, 2'-H$_2$, 3'-H$_2$, 5'-H$_2$, 6'-H$_2$); m/z (%) 376 (46, M$^+$), 278 (20), 260 (100), 232 (22); ν$_{max}$ (KBr disc)/cm$^{-1}$ 1653, 1306, 1234.

EXAMPLE 17 trans-4-tert-Butyldiphenylsilyloxycyclohexyl 3,4-dimethylpyrrolo[3,2-b]carbazole-2-carboxylate was obtained from the reaction of the imidazolide intermediate with trans-4-(tert-butyldiphenylsilyloxy)cyclohexanol (prepared as a mixture with its cis isomer by the reaction of 1,4-cyclohexanediol with tert-butyldiphenylsilyl chloride and imidazole in DMF at room temperature, followed by separation by chromatography) on a 1.5 mmol scale with the addition of catalytic sodium methoxide. Chromatography (gradient elution with ethyl acetate/petrol, 10%–60%) gave a yellow solid (0.389 g, 42%). Recrystallisation of a portion from ethyl acetate gave a yellow solid with m.p. 229°–231° C. (decomp.) (Found: C, 74.21; H, 7.15; N, 4.16. C$_{39}$H$_{42}$N$_2$O$_3$Si.H$_2$O requires: C, 74.02; H, 7.01; N, 4.43%); δH [$^2$H$_6$]-DMSO 11.01 (1H, s, 1-NH), 10.57 (1H, s, 5-NH), 8.03 (1H, d, J 8, 9-H), 7.83 (1H, s, 10-H), 7.57–7.72 (4H, m, 2×2"-H, 2×6"-H), 7.26–7.55 (8H, m, 6-H, 7-H, 2×3"-H, 2×4"-H, 2×5"-H), 7.05 (1H, ddd, J 8, 5, 2, 8-H), 4.99–5.12 (1H, m, 1'-H), 3.82–3.97 (1H, m, 4'-H), 2.85 and 2.87 (2×3H, 2×s, 3-CH$_3$ and 4-CH$_3$), 1.75–2.15 (4H, m, 2'-Heq, 3'-Heq, 5'-Heq, 6'-Heq), 1.40–1.65 (4H, m, 2'-Hax, 3'-Hax, 5'-Hax, 6'-Hax), 1.02 (9H, s, C(CH$_3$)$_3$); m/z (%) 614 (45, M$^+$), 459 (28), 278 (78), 260 (100), 232 (28), 199 (99), 43 (73); ν$_{max}$ (KBr disc)/cm$^{-1}$ 3334, 1655, 1236, 1090.

EXAMPLE 18 trans-4-Hydroxycyclohexyl 3,4-dimethylpyrrolo[3, 2-b]carbazole-2-carboxylate trans-4-tert-Butyldiphenylsilyloxycyclohexyl 3,4-dimethylpyrrolo[3,2-b]carbazole-2-carboxylate (0.246 g, 0.40 mmol) was dissolved in freshly distilled THF (3.8 ml) under a nitrogen atmosphere and treated with a solution of tetra-n-butyl ammonium fluoride in THF (1.0M, 1.2 ml, 1.2 mmol). This mixture was heated to reflux for 3 hours, by which time TLC showed complete disappearance of the starting material. The reaction mixture was partitioned between ethyl acetate and water, and the organic layer was washed with brine. The aqueous layer was further extracted with ethyl acetate. The organic extracts were combined, dried (MgSO$_4$), and concentrated in vacuo to a yellow solid. Chromatography (gradient elution with ethyl acetate/petrol, 40%–75%) gave a yellow solid (0.104 g, 67%) with m.p. 220°–222° C. (decomp.) (Found: C, 71.30; H, 6.76; N, 6.91. C$_{23}$H$_{24}$N$_2$O$_3$.0.7H$_2$O requires: C, 71.00; H, 6.58; N, 7.20%); δH [$^2$H$_6$]-DMSO 11.10 (1H, s, 1-NH), 10.60 (1H, s, 5-NH), 8.08 (1H, d, J 8, 9-H), 7.89 (1H, s, 10-H), 7.31–7.47 (2H, m, 6-H, 7-H), 7.08 (1H, ddd, J 8, 6, 2.5, 8-H), 4.99 (1H, tt, J 8.5, 4, 1'-H), 4.61 (1H, br s, 4'-OH), 3.55–3.70 (1H, m, 4'-H), 2.91 and 2.90 (2×3H, 2×s, 3-CH$_3$ and 4-CH$_3$), 1.83–2.15 (2H, m, 2'-Heq, 6'-Heq), 1.21–1.80 (6H, m, 2'-Hax, 3-CH$_2$, 5-CH$_2$, 6'-Hax); m/z (%) 376 (42, M$^+$), 278 (30), 260 (100), 232 (25); ν$_{max}$ (KBr disc)/cm$^{-1}$ 1668, 1660, 1236.

C: Heterocycloalkyl and Substituted Esters

EXAMPLE 19

Tetrahydro-2H-pyran-4-yl 3,4-dimethylpyrrolo[3,2-b]carbazole-2-carboxylate was obtained from the reaction of the imidazolide intermediate with tetrahydro-4H-pyran-4-ol with the addition of catalytic sodium methoxide. Chromatography (gradient elution with ethyl acetate/petrol, 10%–50%) gave a yellow solid (0.210 g, 58%). A portion was recrystallised from ethyl acetate to gave fine yellow crystals with m.p. 240°–241° C. (decomp.) (Found: C, 71.68; H, 6.07; N, 7.35. $C_{22}H_{22}N_2O_3.0.4H_2O$ requires: C, 71.49; H, 6.22; N, 7.58%); $\delta H$ [$^2H_6$]-DMSO 11.13 (1H, s, 1-NH), 10.60 (1H, s, 5-NH), 8.06 (1H, d, J 7.5, 9-H), 7.88 (1H s, 10-H), 7.30–7.42 (2H, m, 6-H, 7-H), 7.07 (1H, ddd, J 7.5, 6, 1.5, 8-H), 5.20 (1H, tt, J 8, 4, 4'-H), 3.87–3.98 (2H, m, 2'-Heq, 6'-Heq), 3.57 (2H, ddd, J 11.5, 8.5, 3.0, 2'-Hax, 6'-Hax), 2.90 (6H, s, 3-CH$_3$ and 4-CH$_3$), 1.97–2.13 (2H, m, 3'-Heq, 5'-Heq), 1.64–1.83 (2H, m, 3'-Hax, 5'-Hax); m/z (%) 362 (83, M$^+$), 278 (25), 260 (100), 232 (59), 204 (25), 55 (30); $v_{max}$ (KBr disc)/cm$^{-1}$ 3334, 1670, 1236.

EXAMPLE 20

1-Benzylpiperidin-4-yl 3,4-dimethylpyrrolo[3,2-b]carbazole-2-carboxylate was obtained from the reaction (2 mmol scale) of the imidazolide intermediate with 1-benzyl4-hydroxypiperidine (1.5 eq.) with the addition of catalytic sodium methoxide. Chromatography (gradient elution with ethyl acetate/petrol, 20%–60%) gave a yellow solid (0.498 g, 55%). A portion was recrystallised from ethyl acetate to give a yellow solid with m.p. 252°–253° C. (decomp.) (Found: C, 77.84; H, 6.44; N, 9.18. $C_{29}H_{29}N_3O_2$ requires: C, 77.14; H, 6.47; N, 9.31%); $\delta H$ [$^2H_6$]-DMSO 11.12 (1H, s, 1-NH), 10.60 (1H, s, 5-NH), 8.07 (1H, d, J 7.5, 9-H), 7.89 (1H, s, 10-H), 7.19–7.48 (7H, m, 6-H, 7-H, 5×PhH), 7.09 (1H, ddd, J 8, 6, 2, 8-H), 5.05 (1H, tt, J 9, 4, 4'-H), 3.54 (2H, s, PhCH$_2$), 2.89 and 2.90 (2×3H, 2×s, 3-CH$_3$ and 4-CH$_3$), 2.65–2.80 (2H, m, 2'-Heq, 6'-Heq), 2.25–2.42 (2H, m, 2'-Hax, 6'-Hax), 1.90–2.09 (2H, m, 3'-Heq, 5'-Heq), 1.6914 1.90 (2H, m, 3'-Hax, 5'-Hax); m/z (%) 451 (100, M$^+$), 278 (50), 260 (86), 233 (58), 174 (95), 91 (89); $v_{max}$ (KBr disc)/cm$^{-1}$ 3331, 1666, 1238.

EXAMPLE 21

Piperidin-4-yl 3,4-dimethylpyrrolo[3,2-b]carbazole-2-carboxylate was obtained by the reaction of 1-benzylpiperidin-4-yl 3,4-dimethylpyrrolo[3,2-b]carbazole-2-carboxylate (0.339 g, 0.75 mmol) with cyclohexene in the presence of 10% Pd-C (10% by mass) in refluxing THF (transfer hydrogenation). A large excess of cyclohexene was used, added periodically over 24 hours by which time TLC showed no remaining starting material. The reaction mixture was filtered through Hyflo, and the resulting filtrate and washings were concentrated in vacuo to a yellow solid Recrystallisation from THF gave a yellow-orange solid with m.p. 231°–233° C. (decomp.) (Found: C, 71.28; H, 6.70; N, 10.17. $C_{22}H_{23}N_3O_2.0.5H_2O.0.5THF$ requires: C, 70.91; H. 6.94; N, 10.34%); $\delta H$ [$^2H_6$]-DMSO 11.14 (1H, s, 1-NH), 10.60 (1H, s, 5-NH), 8.08 (1H, d, J 7.5, 9-H), 7.89 (1H, s, 10-H), 7.30–7.47 (2H, m, 6-H, 7-H), 7.08 (1H, ddd, J 7.5, 6, 2, 8-H), 5.06 (1H, tt, J 9, 4, 4'-H), 3.62 (2H, t, J 6, 4H of THF), 3.37 (v br s, H$_2$O, NH), 2.93–3.10 (2H, m, 2'-Heq, 6'-Heq), 2.91 (6H, s, 3-CH$_3$ and 4-CH$_3$), 2.65 (2H, br t, J 10, 2'-Hax, 6'-Hax), 1.50–2.00 (ca 6H, m, 3'-H$_2$, 5'-H$_2$, 4H of THF); m/z (%) 361 (42, M$^+$), 278 (48), 260 (100), 232 (28); $v_{max}$ (KBr disc)/cm$^{-1}$ 1670, 1234.

EXAMPLE 22

1-Methylpiperidin-4-yl 3,4-dimethylpyrrolo[3,2-b]carbazole-2-carboxylate was obtained from the reaction of the imidazolide intermediate with 4-hydroxy-N-methylpiperidine with the addition of catalytic sodium methoxide. Chromatography (gradient elution with methanol/DCM, 5%–50%) gave a yellow solid contaminated with imidazole. Recrystallisation from THF/water gave a yellow solid (0.093 g, 23%) with m.p. 278°–280° C. (decomp.) (Found: C, 69.50; H, 6.85; N, 10.42. $C_{23}H_{25}N_3O_2.1.2H_2O$ requires: C, 69.57; H, 6.95; N, 10.58%); $\delta H$ [$^2H_6$]-DMSO 11.10 (1H, s, 1-NH), 10.60 (1H, s, 5-NH), 8.08 (1H, d, J 7.5, 9-H), 7.90 (1H, s, 10-H), 7.30–7.46 (2H, m, 6-H, 7-H), 7.08 (1H, ddd, J 8, 6, 2, 8-H), 4.99 (1H, tt, J 8, 4, 4'-H), 2.90 (6H, s, 3-CH$_3$ and 4-CH$_3$), 2.55–2.75 (2H, m, 2'-Heq, 6'-Heq), .220–2.42 (2H, m, 2'-Hax, 6'-Hax), 2.21 (3H, s, 1'-N—CH$_3$), 1.68–2.10 (4H, m, 3'-H$_2$, 5'-H$_2$); m/z (%) 396 (97, M+M$^+$), 261 (38), 233 (20), 98 (100); $v_{max}$ (KBr disc)/cm$^{-1}$ 3331, 1666, 1238.

EXAMPLE 23

(3,4-Dimethylpyrrolo[3,2-b]-2-carbazolyl) 3O-(1,2:5,6-di-O-isopropylideneglucofuranoside) was obtained from the standard reaction of the imidazolide intermediate with 1,2:5,6-di-O-isopropylidene-D-glucose, with the addition of catalytic sodium methoxide (0.1 eq.). Chromatography (gradient elution with ethyl acetate/petrol, 25%–50%) gave the product as a yellow glassy material (0.439 g, 84%) with m.p. 152°–154° C. (decomp.) (Found: C, 66.56; H. 6.45; N, 5.14. $C_{29}H_{32}N_2O_7$ requires: C, 66.91; H, 6.20; N, 5.38%); $\delta H$ [$^2H_6$]-DMSO 11.17 (1H, s, 1-NH), 10.62 (1H, s, 5-NH), 8.06 (1H, d, J 7.5, 9-H), 7.90 (1H, s, 10-H), 7.31–7.43 (2H, m, 6-H, 7-H), 7.07 (1H, ddd, J 7.5, 6, 2, 8-H), 6.03 (1H, d, J 3.5, 1'-H), 5.35 (1H, d, J 3, 3'-H), 4.74 (1H, d, J 4, 2'-H), 4.52 (1H, q, J 6, 5'-H), 4.23 (1H, dd, J 8, 3, 4'-H), 3.93–4.17 (2H, m, 6'-H$_2$), 2.90 and 2.89 (2×3H, 2×s, 3-CH$_3$ and 4-CH$_3$), 1.49, 1.35, 1.29 and 1.21 (4×3H, 4×s, 2×(CH$_3$)$_2$C); m/z (%) 520 (82, M$^+$), 260 (100); $v_{max}$ (KBr disc)/cm$^{-1}$ 1699, 1231.

EXAMPLE 24

(3,4-Dimethylpyrrolo[3,2-b]-2-carbazolyl) 3-O-(1,2-O-isopropylideneglucofuranoside) was obtained by the hydrolysis of (3,4-dimethylpyrrolo[3,2-b]-2-carbazolyl) 3-O-(1,2:5,6-di-O-isopropylideneglucofuranoside (0.5 mmol) using catalytic tosic acid (0.2 eq.) in methanol at room temperature. Chromatography (gradient elution with ethyl acetate/petrol, 50%–100%, then 10% methanollethyl acetate) gave the product as a yellow solid (0.220 g, 92%). Recrystallisation from ethyl acetate gave yellow crystals with m.p. 231°–233° C. (decomp.) (but discoloured gradually above 190° C.) (Found: C, 63.44; H, 5.80; N, 5.40. $C_{26}H_{28}N_2O_7.0.7H_2O$ requires: C, 63.32; H, 6.01; N, 5.68%); $\delta H$ [$^2H_6$]-DMSO 11.17 (1H, s, 1-NH), 10.61 (1H, s, 5-NH), 8.08 (1H, d, J 7.5, 9-H), 7.92 (1H, s, 10-H), 7.31–7.48 (2H, m, 6-H, 7-H), 7.09 (1H, ddd, J 8, 6, 3, 8-H), 6.00 (1H, d, J 5, 1'-H), 5.40 (1H, d, J 4, 3'-H), 4.86 (1H, d, J 6, 2'-H), 4.69 (1H, d, J 4, 5'-OH), 4.55 (1H, d, J 5, 6'-OH), 4.25 (1H, dd, J 9, 4, 4'-H), 3.88–3.99 (1H, m, 5'-H), 3.59–3.72 (1H, m, 6'-H), 3.40–3.55 (1H, m, 6'-H), 2.91 and 2.90 (2×3H, 2×s, 3-CH$_3$ and 4-CH$_3$), 1.49 and 1.30 (2×3H, 2×s, (CH$_3$)$_2$C); m/z (%) 480 (70, M$^+$), 278 (73), 260 (100), 231 (42); $v_{max}$ (KBr disc)/cm$^{-1}$ 3396, 1695, 1234.

D: Substituted Aryl Esters

EXAMPLE 25

[3-(4-Nitrophenylmethoxy)phenyl] 3,4-dimethylpyrrolo[3,2-b] carbazole-2-carboxylate was obtained from the standard reaction of the imidazolide intermediate with 3-(4- nitrophenylmethoxy)phenol. Due to insolubility the material could not be purified by chromatography. The residue from the reaction (after removal of solvent) was redissolved in THF and precipitated with petrol to give the product as a brown powder (two crops totalling 0.438 g, 86%) with m.p. 254°–256° C. (decomp.) (Found: C, 71.36; H, 4.80; N, 8.07. $C_{30}H_{23}N_3O_5$ requires: C, 71.28; H, 4.59; N, 8.31%); δH [$^2H_6$]-DMSO 11.53 (1H, s, 1-NH), 10.65 (1H, s, 5-NH), 8.29 (2H, d, J 9.5, 3"-H, 5"-H) 8.09 (1H, d, J 8, 9-H), 7.92 (1H, s, 10-H), 7.76 (2H, d, J 9.5, 2"-H, 6"-H), 7.34–7.48 (3H, m, 6-H, 7-H, 5'-H), 6.91–7.14 (4H, m, 8-H, 2'-H, 4'-H, 6'-H), 5.37 (2H, s, $OCH_2$), 2,96 and 2.94 (2×3H, 2×s, 3-$CH_3$ and 4-$CH_3$); m/z (%) 505 (25, M$^+$), 370 (25), 261 (100), 233 (35); $v_{max}$ (KBr disc)/cm$^{-1}$ 3339, 1684, 1180.

EXAMPLE 26

(3-Hydroxyphenyl) 3,4-dimethylpyrrolo[3,2-b]carbazole-2-carboxylate was obtained by the catalytic hydrogenation of [3-(4-nitrophenylmethoxy)phenyl] 3,4-dimethylpyrrolo[3,2-b]carbazole-2-carboxylate (0.253g, 0.5 mmol) in THF (10 ml) using 10% Pd-C (20% by mass) for 7 h at atmospheric pressure. The reaction mixture was filtered through Hyflo to remove the catalyst, washing with excess THF, and the combined filtrate and washings were concentrated to a yellow solid. Chromatography (gradient elution with ethyl acetate/petrol, 25%–40%) followed by recrystallisation from ethyl acetate-petrol gave the product as a yellow powder (0.122 g, 66%) with m.p. 267°–269° C. (decomp.) (Found: C, 73.57; H, 4.81; N, 7.26. $C_{23}H_{18}N_2O_3.0.3H_2O$ requires: C, 73.51; H, 4.99; N, 7.45%); δH [$^2H_6$]-DMSO 11.50 (1H, s, 1-NH), 10.14 (1H, s, 5-NH), 9.25 (1H, v br s, OH), 8.08 (1H, d, J 7.5, 9-H), 7.90 (1H, s, 10-H), 7.22–7.43 (3H, m, 6-H, 7-H, 5'-H), 7.08 (1H, ddd, J 8, 6, 2, 8-H), 6.70–6.76 (3H, m, 2'-H, 4'-H, 6'-H), 2.96 and 2.94 (2×3H, 2×s, 3-$CH_3$ and 4-$CH_3$); m/z (%) 370 (8, M$^+$), 261 (8), 43 (100); $v_{max}$ (KBr disc)/cm$^{-1}$ 3391, 1732, 1695, 1234.

EXAMPLE 27

(4-Phthalamidophenyl) 3,4-dimethylpyrrolo[3,2-b]carbazole-2-carboxylate was obtained from the standard reaction of the imidazolide intermediate with N-p-hydroxyphenylphthalimide. Due to insolubility the material could not be purified by chromatography. The impure material from the attempted column was recrystallised from THF to give the product as an orange powder (three crops totalling 0.304 g, 60%), which did not melt properly, but discoloured above 240° C. (Found: C, 71.95; H, 4.10; N, 7.96. $C_{31}H_{21}N_3O_4.H_2O$ requires: C, 71.94; H, 4.48; N, 8.12%); δH [$^2H_6$]-DMSO 11.58 (1H, s, 1-NH), 10.65 (1H, s, 5-NH), 8.10 (1H, d, J 8, 9-H), 7.90–8.05 (5H, m, 10-H, 3"-H, 4"-H, 5"-H, 6"H), 7.35–7.64 (6H, m, 6-H, 7-H, 2'-H, 3'-H, 5'-H, 6'-H), 7.10 (1H, ddd, J 7, 6, 2, 8-H), 2.99 and 2.95 (2×3H, 2×s, 3-$CH_3$ and 4-$CH_3$); m/z (%) 499 (45, M$^+$), 261 (100); $v_{max}$ (KBr disc)/cm$^{-1}$ 3418, 1713, 1236.

EXAMPLE 28

4-(Aminophenyl) 3,4-dimethylpyrrolo[3,2-b]carbazole-2-carboxylate was obtained by the reaction of (4-phthalamidophenyl)-3,4-dimethylpyrrolo[3,2-b]carbazole-2-carboxylate (0.206 g, 0.412 mmol) with hydrazine hydrate (10 eq.) in ethanol (8 ml) at reflux for 1 h. The reaction mixture was allowed to cool and diluted with THF. This mixture was filtered to remove a cream solid (presumed phthalazine), and the resulting yellow filtrate was concentrated to a yellow solid. Chromatography (gradient elution with ethyl acetate/petrol, 25%–100%) followed by recrystallisation from THF-petrol gave the product as a yellow powder (0.063 g, 40%) which did not melt up to 330° C.; (Found: C, 72.90; H, 5.08; N, 10.92. $C_{23}H_{19}N_3O_2.0.5H_2O$ requires: C, 73.00; H, 5.33; N, 11.10%); δH [$^2H_6$]-DMSO 11.45 (1H, s, 1-NH), 10.64 (1H, s, 5-NH), 8.09 (1H, d, J 8.5, 9-H), 7.91 (1H, s, 10-H), 7.32–7.48 (2H, m, 6-H, 7-H), 7.10 (1H, ddd, J 8.5, 6, 2.5, 8-H), 6.97 (2H, d, J 9, 2'-H, 6'-H), 6.65 (2H, d, J 9, 3'-H, 5'-H), 5.09 (2H, br s, $NH_2$), 2.95 and 2.94 (2×3H, 2×s, 3-$CH_3$ and 4-$CH_3$); m/z (%) 369 (42, M$^+$), 261 (100), 233 (40); $v_{max}$ (KBr disc)/cm$^{-1}$ 3388, 1707, 1182.

EXAMPLE 29

(4-Nitrophenylmethyl) 3-(3,4-dimethylpyrrolo[3,2-b]carbazole-2-carboxy)benzoate was obtained from the standard reaction of the imidazolide intermediate with 4-nitrobenzyl-3-hydroxybenzoate. Due to insolubility the material could not be purified by chromatography. The residue from the reaction (after removal of solvent) was recrystallised from acetone to give the product as an orange powder (four crops totalling 0.851 g, 84%) with m.p. 263°–265° C. (decomp.) (Found: C, 68.34; H, 4.29; N, 7.51. $C_{31}H_{23}N_3O_6.0.6H_2O$ requires: C, 68.40; H, 4.48; N, 7.72%); δH [$^2H_6$]-DMSO 11.58 (1H, s, 1-NH), 10.66 (1H, s, 5-NH), 8.29 (2H, d, J 9, 3"-H, 5"-H), 8.11 (1H, d, J 8, 9-H), 7.93–8.08 (3H, m, 10-H, 2'-H, 4'-H), 7.79 (2H, d, J 9, 2"-H, 6"-H), 7.68–7.75 (2H, m, 5'-H, 6'-H), 7.33–7.49 (2H, m, 6-H, 7-H), 7.09 (1H, ddd, J 8, 6, 2, 8-H), 5.55 (2H, s, $CO_2OCH_2$), 2.99 and 2.95 (2×3H, 2×s, 3-$CH_3$ and 4-$CH_3$); m/z (%) 533 (1M$^+$), 378 (40), 243 (100); $v_{max}$ (KBr disc)/cm$^{-1}$ 3362, 1717, 1686, 1289.

EXAMPLE 30

3-(3,4-dimethylpyrrolo[3,2-b]carbazole-2-carboxy)benzoic acid was obtained by the catalytic hydrogenation of (4-nitrophenylmethyl) 3-(3,4-dimethylpyrrolo[3,2-b]carbazole-2-carboxy)benzoate (0.267 g, 0.5 mmol) in THF (10 ml) using 10% Pd-C (10% by mass) for 2 h at atmospheric pressure. The reaction mixture was filtered through Hyflo to remove the catalyst, washing with excess THF, and the combined filtrate and washings were concentrated to a yellow solid. Chromatography (gradient elution with ethyl acetate/petrol, 50%–100% then with methanol/ethyl acetate, 5%–50%) followed by recrystallisation from TeF-petrol gave the product as a yellow powder (0.185 g, 9%) which did not melt up to 300° C. (but discoloured gradually above 260° C.); δH [$^2H_6$]-DMSO 11.56 (1H, s, 1-NH), 10.68 (1H, s, 5- NH), 8.09 (1H, d, J 7.5, 9-H), 7.99 (1H, s, 10-H), 7.87 (2H, d, J 9, 2'-H, 4'-H), 7.32–7.52 (4H, m, 6-H, 7-H, 5'-H, 6'-H), 7.10 (1H, ddd, J 8, 6.5, 1.5, 8-H), 2.99 and 2.95 (2×3H, 2×s, 3-$CH_3$ and 4-$CH_3$); m/z (%) 398 (52, M$^+$), 261 (100), 233 (50); $v_{max}$ (KBr disc)/cm$^{-1}$ 3369, 1697, 1213; (Found: M$^+$ 98.1265, $C_{24}H_{18}N_2O_4$ requires 398.1267).

EXAMPLE 31

3-(tert-Butyldiphenylsilyloxymethyl)phenyl 3,4-dimethylpyrolo[3,2-b]carbazole-2-carboxylate was obtained from the reaction of the imidazolide intermediate with 3-(tert-butyldiphenynsilyloxymethyl)phenol (prepared by the reaction of 3-hydroxybenzyl alcohol with tert-butygdiphenylsilyl chloride and imidazole in DMF at room temperature) on a 1.5 mmol scale. Chromatography (gradient elution with ethyl acetate/petrol, 10%–30%) gave a yellow solid (0.671 g, 71%). Recrystallisation of a portion from ethyl acetate/petrol gave bright yellow crystals with m.p. 188°–190° C. (decomp.) (Found: C, 77.02; H, 6.07; N, 4.44. $C_{40}H_{38}N_2O_3Si$ requires: C, 77.14; H, 6.15; N, 4.50%);

δH [²H₆]-DMSO 11.54 (1H, s, 1-NH), 10.64 (1H, s, 5-NH), 8.09 (1H, d, J 8.5, 9-H), 7.91 (1H, s, 10-H), 7.60–7.75 (4H, m, 2×2"-H, 2×6"-H), 7.18–7.58 (12H, m, 6-H, 7-H, 2'-H, 4'-H, 5'-H, 6'-H, 2×3"-H, 2×4"-H, 2×5"-H), 7.09 (1H, ddd, J 8.5, 6.5, 2, 8-H), 4.36 (2H, s, CH₂O), 2.97 and 2.95 (2×3H, 2×s, 3-CH₃ and 4-CH₃), 1.07 (9H, s, C(CH₃)₃); m/z (%) 622 (48, M⁺), 487 (40), 305 (30), 261 (100), 233 (46); ν$_{max}$ (KBr disc)/cm⁻¹ 1651, 1230, 1107.

EXAMPLE 32

(3-Hydroxymethyl)phenyl 3,4-dimethylpyrrolo[3,2-b]carbazole-2-carboxylate 3-(tert-Butyldiphenylsilyloxymethyl)phenyl 3,4-dimethylpyrrolo[3,2-b]carbazole-2-carboxylate (0.498 g, 0.80 mmol) was dissolved in freshly distilled THF (7 ml) under a nitrogen atmosphere and treated with a solution of tetra-n-butyl ammonium fluoride in THF (1.1M, 3 ml, 3.3 mmol). This mixture was stirred at room temperature for 1.5 hours, by which time TLC showed complete disappearance of the starting material. The reaction mixture was partitioned between ethyl acetate and water, and the organic layer was washed with brine. The aqueous layer was further extracted with ethyl acetate. The organic extracts were combined, dried (MgSO₄), and concentrated in vacuo to a yellow solid. Chromatography (gradient elution with ethyl acetate/petrol, 20%–100%, then 5% methanol/ethyl acetate) gave a yellow solid (0.216 g, 70%) with m.p. 246°–248° C. (decomp.) (Found: C, 74.75; H, 5.24 N, 7.11. C₂₄H₂₀N₂O₃ requires: C, 74.98; H, 5.24; N, 7.29%); δH [²H₆]-DMSO 11.54 (1H, s, 1-NH), 10.67 (1H, s, 5-NH), 8.11 (1H, d, J 8, 9-H), 7.95 (1H, s, 10-H), 7.15–7.50 (6H, m, 6-H, 7-H, 2'-H, 4'-H, 5'-H, 6'-H), 7.09 (1H, ddd, J 7.5, 6, 2, 8-H), 5.34 (1H, t, J 5.5, O—H), 4.60 (2H, s, CH₂OH), 2.96 and 2.98 (2×3H, 2×s, 3-CH₃ and 4-CH₃); m/z (%) 384 (48, M⁺), 261 (100), 233 (60); ν$_{max}$ (KBr disc)/cm⁻¹ 1752, 1227, 1188.

EXAMPLE 33

[3-(4-Nitrophenylmethoxy)phenyl]4-methyl-1H-[1]benzothieno[2,3-f]indole-2-carboxylate 1,1-Carbonyl diimidazole (0.187 g, 1.15 mmol) and 4-methyl-1H-[1]benzothieno[2,3-f]indole-2-carboxylic acid (0.28 g, 1.0 mmol) were mixed in dry THF (10 ml) and stirred under a nitrogen atmosphere for 2.5 h. 3-(4-Nitrophenylmethoxy)phenol (0.366 g, 1.5 mmol) was added and the reaction was heated to reflux for 48 h. The reaction mixture was allowed to cool, filtered, and the residue was washed with THF. The solvent was removed from the combined filtrate and washings and the resulting yellow solid was triturated with ethyl acetate/petrol (1:1). Recrystallisation from toluene gave the product as yellow crystals (0.275 g, 54%) with m.p. 254°–255° C; (Found: C, 68.37; H, 3.95; N, 5.41. C₂₉H₂₀N₂O₅S requires: C, 68.49; H. 3.96; N, 5.51%); δH [²H₆]-DMSO 12.35 (1H, s, 1-NH), 8.20–8.40 (4H, m, 9-H, 10-H, 3"-H, 5"-H), 7.94–8.00 (1H, m, 6-H), 7.75 (2H, d, J 9, 2"-H, 6"-H), 7.63 (1H, d, J 2, 3-H), 7.38–7.55 (3H, m, 7-H, 8-H, 5'-H), 6.95–7.15 (3H, m, 2'-H, 4'-H, 6'-H), 5.35 (2H, s, OCH₂), 2.79 (3H, s, 4-CH₃); m/z (%) 508 (6, M⁺), 373 (15), 264 (44), 236 (12), 91 (100); ν$_{max}$ (KBr disc)/cm⁻¹ 3356, 1707.

EXAMPLE 34

(3-Hydroxyphenyl)4-methyl-1H-[1]benzothieno[2,3-f]indole-2-carboxylate was obtained by the catalytic hydrogenation of [3-(4-Nitrophenylmethoxy)phenyl]4-methyl-1H-[1]benzothieno[2,3-f]indole-2-carboxylate (0.100 mg, 0.20 mmol) in THF (11 ml) using 10% Pd-C (30% by mass) for 20 h at atmospheric pressure. The reaction mixture was filtered through Hyflo to remove the catalyst, washing with excess THF, and the combined filtrate and washings were concentrated to a yellow solid. Recrystallisation from toluene gave the product as a yellow solid (0.040 g, 54%) with m.p. 224°–225° C.; (Found: C, 70.65; H, 3.97; N, 3.75. C₂₂H₁₅NO₃S requires: C, 70.76; H, 4.05; N, 3.75%); δH [²H₆]-DMSO 12.32 (1H, s, 1-NH), 9.78 (1H, br s, OH), 8.30–8.38 (1H, m, 9-H), 8.22 (1H, s, 10-H), 7.93–8.02 (1H m, 6-H), 7.63 (1H, s, 3-H), 7.45–7.58 (2H, m, 7-H, 5'-H), 7.03–7.35 (1H, m, 8-H), 6.69–6.80 (3H, m, 2'-H, 4'-H, 6'-H), 2.76 (3H, s, 4-CH₃); m/z (%) 373 (52, M⁺), 264 (100), 236 (22), 209 (42); ν$_{max}$ (KBr disc)/cm⁻¹ 3346, 1707, 1192.

E: Substituted Aralkyl Esters

EXAMPLE 35

3-(4-Nitrophenylmethoxy)phenylmethyl 3,4-dimethylpyrrolo[3,2-b]carbazole-2-carboxylate was obtained from the reaction of the imidazolide intermediate with 3-(4-nitrophenylmethoxy)phenylmethanol. Chromatography (gradient elution with ethyl acetate/petrol, 30%–50%) gave a dark orange solid (0.341 g, 65%). Recrystallisation of a portion from THF/petrol gave an orange solid with m.p. 233°–235° C. (decomp.) (Found: C, 71.99; H, 5.13; N, 7.90. C₃₁H₂₅N₃O₅ requires: C, 71.67; H, 4.85; N, 8.09%); δH [²H₆]-DMSO 11.27 (1H, s, 1-NH), 10.62 (1H, s, 5-NH), 8.24 (2H, d, J 9.5, 3"-H, 5"-H), 8.08 (1H, d, J 8, 9-H), 7.89 (1H, s, 10-H), 7.74 (2H, d, J 9, 2"-H, 6"-H), 7.32–7.45 (3H, m, 6-H, 7-H, 5'-H), 7.00–7.25 (4H, m, 8-H, 2'-H, 4'-H, 6'-H), 5.33 and 5.39 (2×2H, 2×s, 2×OCH₂), 2.89 and 2.92 (2×3H, 2×s, 3-CH₃ and 4-CH₃); m/z (%) 520 (21, M+1⁺), 391 (23), 232 (70), 197 (72); ν$_{max}$ (KBr disc)/cm⁻¹ 1676, 1346, 1231.

EXAMPLE 36

3-(tert-Butyldiphenylsilyloxyphenyl)methyl 3,4-dimethylpyrrolo[3,2-b]carbazole-2-carboxylate was obtained from the reaction of the imidazolide intermediate with 3-(tert-butyldiphenylsilyloxy-phenyl)methanol (prepared by the reaction of 3-hydroxybenzyl alcohol with tert-butyldiphenylsilyl chloride and 1,8-diazabicyclo[5.4.0]undec-7-ene in DCM at room temperature). Chromatography (gradient elution with ethyl acetate/petrol, 10%–50%) followed by recrystallisation from diethyl ether/petrol gave yellow crystals with m.p. 143°–145° C. (Found: C, 77.27; H, 6.08; N, 4.35. C₄₀H₃₈N₂O₃Si requires: C, 77.14; H, 6.15; N, 4.50%); δH [²H₆]-DMSO 11.21 (1H, s, 1-NH), 10.61 (1H, s, 5-NH), 8.09 (1H, d, J 8, 9-H), 7.90 (1H, s, 10-H), 7.62–7.70 (4H, m, 2×2"-H, 2×6"-H), 7.31–7.46 (8H, m, 6-H, 7-H, 2×3"-H, 2×4"-H, 2×5"-H), 7.19 (1H, t, J7.5, 5'-H), 6.97–7.13 (3H, m, 8-H, 2'-H, 6'-H), 6.68 (1H, dt, J 7.5, 2, 4'-H), 5.28 (2H, s, CH₂O), 2.91 and 2.81 (2×3H, 2×s, 3-CH₃ and 4-CH₃), 1.07 (9H, s, C(CH₃)₃); m/z (%) 623 (100, M+1⁺), 232 (39), 197 (37); ν$_{max}$ (KBr disc)/cm⁻¹ 1684, 1308, 1284, 1232.

EXAMPLE 37

(3-Hydroxyphenyl)methyl 3,4-dimethylpyrrolo[3,2-b]carbazole-2-carboxylate 3-(tert-Butyldiphenylsilyloxyphenyl)methyl 3,4-dimethylpyrrolo[3,2-b]carbazole-2-carboxylate (0.311 g, 0.50 mmol) was dissolved in freshly distilled THF (4 ml)

under a nitrogen atmosphere and treated with a solution of tetra-n-butyl ammonium fluoride in THF (1.0M, 1.0 ml, 1.0 mmol). This mixture was stirred at room temperature for 1.5 hours, by which time TLC showed complete disappearance of the starting material. The reaction mixture was partitioned between ethyl acetate and water, and the organic layer was washed with brine. The aqueous layer was further extracted with ethyl acetate. The organic extracts were combined, dried (MgSO$_4$), and concentrated in vacuo to a yellow oil. Chromatography (gradient elution with ethyl acetate/petrol, 10%–33%) followed by recrystallisation from ethyl acetate gave a yellow solid (0.070 g, 35%) with m.p. 213°–215° C. (decomp.) (Found: C, 71.91; H, 5.87 N, 6.70. C$_{24}$H$_{20}$N$_2$O$_3$.H$_2$O requires: C, 71.63; H, 5.51; N, 6.96%); δH [$^2$H$_6$]-DMSO 11.26 (1H, s, 1-NH), 10.61 (1H, s, 5-NH), 9.49 (1H, br s, OH), 8.07 (1H, d, J 7.5, 9-H), 7.89 (1H, s, 10-H), 7.30–7.47 (2H, m, 6-H, 7-H), 7.22 (1H, t, J 7.5, 5'-H), 7.09 (1H, ddd, J 7.5, 5.5, 2, 8-H), 6.89–6.98 (2H, m, 2'-H, 6'-H), 6.77 (1H, dd, J 8, 3, 4'-H), 5.33 (2H, s, C$\underline{H}_2$OH), 2.92 (6H, s, 3-CH$_3$ and 4-CH$_3$); m/z (%) 384 (4, M$^+$), 260 (12), 231 (5) 142 (100), 100 (75); ν$_{max}$ (KBr disc)/cm$^{-1}$ 3396, 1679, 1234.

F: Substituted Alkyl Amides

EXAMPLE 38

(1-Hydroxy-2-methylpropyl-2) 3,4-dimethylpyrrolo[3,2-b]carbazole-2-carboxamide 3,4-Dimethylpyrrolo[3,2-b]carbazole-2-carboxylic acid (0.556 g, 2.0 mmol) was weighed into an oven-dried flask under nitrogen and dissolved in DMF (10 ml). Carbonyl diimidazole (0.37 g, 2.2 mmol) was added and the mixture stirred at room temperature for 2.5 hours, by which time TLC showed no remaining starting material. 2-Amino-2-methylpropanol (25 g, excess) was added and the resulting mixture was heated to 75°–80° C. for 4 hours, by which time TLC showed no remaining imidazolide intermediate. Water (300 ml) was added, giving an orange precipitate, which was collected by filtration, washed with water and dried. This solid was recrystallised from DMF/water to give the product (0.216 g, 31%) with m.p. 210° C. (decomp.); δH [$^2$H$_6$]-DMSO 10.96 (1H, br s, 1-NH), 10.57 (1H, s, 5-NH), 8.09 (1H, d, J 9, 9-H), 7.83 (1H, s, 10-H), 7.29–7.47 (2H, m, 6-H, 7-H), 7.19 (1H, br s, amide NH), 7.08 (1H, t, J 7.5, 8-H), 4.99 (1H, t, J 5.5, O-H), 3.58 (2H, d, J 5.5, 2'-H$_2$), 2.89 and 2.80 (2×3H, 2×s, 3-CH$_3$ and 4-CH$_3$), 1.39 (6H, s, C(CH$_3$)$_2$); m/z (%) 349 (65, M$^+$), 261 (80), 181 (90), 149 (93), 57 (100); ν$_{max}$ (KBr disc)/cm$^{-1}$ 3331, 1608, 1539, 1309, 1244; (Found: M$^+$ 349.1810, C$_{21}$H$_{23}$N$_3$O$_2$ requires 349.1790).

EXAMPLE 39

2-Hydroxyethyl 3,4-dimethylpyrrolo[3,2-b]carbazole-2-carboxamide

Ethyl 3,4-dimethylpyrrolo[3,2-b]carbazole-2-carboxylate (1.00 g, 3.26 mmol) was suspended in ethanolamine (5 ml) and heated at reflux (giving an orange solution) under nitrogen for 1.5 hours, by which time TLC showed no remaining starting material. The excess ethanolamnine was removed in vacuo and the yellow residue was triturated with DCM. The resulting solid was recrystallised from ethanol/water to give the product (two crops combined) (0.383 g, 36.5%) with m.p. 270° C. (decomp.); δH [$^2$H$_6$]-DMSO 10.90 (1H, br s, 1-NH), 10.59 (1H, s, 5-NH), 8.09 (1H, d, J 9, 9-H), 7.89 (1H, t, J 5, amide NH), 7.85 (1H, s, 10-H), 7.29–7.45 (2H, m, 6-H, 7-H), 7.08 (1H, t, J 7.5, 8-H), 4.80 (1H, t, J 5, O-H), 3.60 (2H, quartet, J 6, 2'-H$_2$), 3.23–3.50 (2H, m, 1'-H$_2$), 2.92 and 2.86 (2×3H, 2×s, 3-CH$_3$ and 4-CH$_3$); m/z (%) 321 (87, M$^+$), 303 (72), 260 (100), 231 (64), 69 (67); ν$_{max}$ (KBr disc)/cm$^{-1}$ 3334, 1587, 1543, 1309, 1250.

EXAMPLE 40

2-Chloroethyl 3,4-dimethylpyrrolo[3,2-b]carbazole-2-carboxamide

2-Hydroxyethyl 3,4-dimethylpyrrolo[3,2-b]carbazole-2-carboxamide (0.70 g, 2.18 mmol) was suspended in carbon tetrachloride (70 ml) under a nitrogen atmosphere and heated to reflux using a Dean-Stark apparatus to remove any water. The Dean-Stark was removed and dry DMF (14 ml) added to give a yellow solution. A solution of triphenylphosphine (1.14 g, 4.36 mmol) in carbon tetrachloride (15 ml) was added, causing the mixture to become an orange suspension. This was heated to reflux for 1.5 hours by which time TLC showed no remaining starting material. The reaction was allowed to cool to room temperature, and the orange solid was collected by filtration, washed with further CCl$_4$ and dried to give the product (0.54 g, 73%); δH [$^2$H$_6$]-DMSO 10.95 (1H, br s, 1-NH), 10.58 (1H, s, 5-NH), 8.25 (1H, t, J 5, amide NH), 8.10 (1H, d, J 9, 9-H), 7.88 (1H, s, 10-H), 7.29–7.46 (2H, m, 6-H, 7-H), 7.08 (1H, t, J 7.5, 8-H), 3.80 (2H, t, J 6, 2'-H$_2$), 3.57–3.70 (2H, m, 1'-H$_2$), 2.90 and 2.85 (2×3H, 2×s, 3-CH$_3$ and 4-CH$_3$); m/z (%) 304 (25, M+1$^-$); ν$_{max}$ (KBr disc)/cm$^{-1}$ 1622, 1329.

EXAMPLE 41

N-(2-Aminoethyl) 3,4-dimethylpyrrolo[3,2-b]carbazole-2-carboxamide

Ethyl 3,4-dimethylpyrrolo[3,2-b]carbazole-2-carboxylate (containing 1 eq.EtOAc, 1.58 g, 4.0 mmol) was suspended in 1,2-diaminoethane (20 ml) under a nitrogen atmosphere and heated to reflux (giving a yellow solution) for 45 hours, by which time TLC showed no remaining starting material. The reaction mixture was allowed to cool and poured into excess water to give a yellow suspension. Filtration gave a yellow solid which was washed with more water and dried at 60° C. in vacuo to give the product (1.307 g, 99%) with m.p. 245°–247° C. (decomp.) (Found: C, 69.07; H, 6.26 N, 17.22. C$_{19}$H$_{20}$N$_4$O.0.5H$_2$O requires: C, 69.28; H, 6.43; N, 17.01%); δH [$^2$H$_6$]-DMSO 10.84 (1H, br s, 1-NH), 10.53 (1H, s, 5-NH), 8.05 (1H, d, J 9, 9-H), 7.86 (1H, br t, J 4, amide NH), 7.83 (1H, s, 10-H), 7.38 (1H, d, J 8.5, 6-H) 7.32 (1H, t, J 7.5, 7-H), 7.05 (1H, t, J 7.5, 8-H), 3.25–3.35 (2H, m, 1'-H$_2$), 3.20 (v br s, H$_2$O, NH$_2$), 2.89 and 2.80 (2×3H, 2×s, 3-CH$_3$ and 4-CH$_3$), 2.74 (2H, t, J 6, 2'-H$_2$); m/z (%) 321 (100, M+1$^+$), 261 (52); ν$_{max}$ (KBr disc)/cm$^{-1}$ 3395, 1626, 1541, 1240.

EXAMPLE 42

N-(2-Acetamidoethyl) 3,4-dimethylpyrrolo[3,2-b]carbazole-2-carboxamide

N-(2-Aminoethyl) 3,4-dimethylpyrrolo[3,2-b]carbazole-2-carboxamide (0.064 g, 0.20 mmol) and 4A molecular seives (0.064 g) were suspended in acetic acid/dioxane (1.0 ml of each) and heated to reflux under a nitrogen atmosphere for 24 hours. The reaction mixture was allowed to cool, filtered to remove the sieves (washing with excess acetic acid) and concentrated in vacuo to a brown solid. This was triturated with a mixture of ethyl acetate and THF to leave a yellow solid (0.036 g, 50%) which decomposed above 280° C. (had darkened above 200° C.); δH [$^2$H$_6$]-DMSO 11.30 (1H, s, 1-NH), 10.49 (1H, s, 5-NH), 8.43 and 8.19 (2×1H, 2×br t, J 4, 2×amide NH), 8.06 (1H, d, J 8, 9-H), 7.81 (1H, s, 10-H), 7.39 (1H, d, J 8, 6-H) 7.32 (1H, t, J 7.5, 7-H), 7.04 (1H, t, J 7.5, 8-H), 3.30–3.40 (4H, m, 1'-H$_2$, 2'-H$_2$), 2.89 and 2.83 (2×3H, 2×s, 3-CH$_3$ and 4-CH$_3$), 1.73 (3H, s, CH$_3$CO); m/z (%) 362 (64, M$^+$), 260 (100), 232 (32), 43 (40); $\nu_{max}$ (KBr disc)/cm$^{-1}$ 3302, 1606, 1545; (Found: M$^+$ 362.1732, C$_{21}$H$_{22}$N$_4$O$_4$ requires 362.1743).

EXAMPLE 43

(3-Aminopropyl-1) 3,4-dimethylpyrrolo[3,2-b]carbazole-2-carboxamide

Ethyl 3,4-dimethylpyrrolo[3,2-b]carbazole-2-carboxylate (containing 1 eq.EtOAc, 0.919 g, 3.0 mmol) was suspended in 1,3-diaminopropane (15 ml) under a nitrogen atmosphere and heated to reflux (giving a yellow solution) for 28 hours, by which time TLC showed no remaining starting material. The reaction mixture was allowed to cool and poured into excess water to give a yellow suspension. Filtration gave a yellow solid which was washed with more water and dried at 60° C. in vacuo. Trituration with methanol removed alot of soluble orange material to give the product as a yellow solid (0.468 g, 47%). Further trituration followed by drying at 60° C. in vacuo gave an analytically pure sample with m.p. 213°–215° C. (decomp.) (Found: C, 70.95; H. 6.46 N, 16.21. C$_{20}$H$_{22}$N$_4$O.0.3H$_2$O requires: C, 70.69; H, 6.70; N, 16.49%); δH [$^2$H$_6$]-DMSO 10.81 (1H, br s, 1-NH), 10.50 (1H, s, 5-NH), 8.07 (1H, d, J 8, 9-H), 7.97 (1H, br t, J 4.5, amide NH), 7.83 (1H, s, 10-H), 7.39 (1H, d, J 8, 6-H) 7.32 (1H, t, J 8, 7-H), 7.07 (1H, t, J 8, 8-H), 3.30–3.45 (2H, m, 1'-H$_2$), 3.25 (v br s, H$_2$O, NH$_2$), 2.89 and 2.82 (2×3H, 2×s, 3-CH$_3$ and 4-CH$_3$), 2.68 (2H, t, J 6, 3'-H$_2$), 1.67 (2H, quintet, J 6.5, 2'-H$_2$); m/z (%) 335 (100, M+1$^+$), 261 (82), 233 (38), 181 (40); $\nu_{max}$ (KBr disc)/cm$^{-1}$ 3298, 1606, 1543, 1311, 1249.

EXAMPLE 44

2-Hydroxyethyl 4-methyl-1H-[1]benzothieno[2,3-f]indole-2-carboxamide

Ethyl 4-methyl-1H-[1]benzothieno[2,3-f]indole-2-carboxylate (500 mg, 1.62 mmol) was mixed with ethanolamine (2 ml) and heated at reflux under nitrogen for one hour. The excess ethanolamine was removed in vacuo and the residue was triturated with ethyl acetate. The resulting solid was recrystallised from DMF/water to give the product (0.390 g, 74%) with m.p. 230°–232° C. (Found: C, 65.64; H, 4.90 N, 8.61. C$_{18}$H$_{16}$N$_2$O$_2$S.0.25H$_2$O requires: C, 65.73; H, 5.06; N, 8.52%); δH [$^2$H$_6$]-DMSO 11.78 (1H, s, 1-NH), 8.55 (1H, t, J 5.5, amide N-H), 8.21–8.31 (1H, m, 9-H), 8.17 (1H, s, 10-H), 7.89–7.99 (1H, m, 6-H), 7.42–7.52 (2H, m, 7-H, 8-H), 7.34 (1H, s, 3-H), 4.79 (1H, t, J 5.5, O-H), 3.59 (2H, quartet, J 6, 2'-H$_2$), 3.42 (2H, quartet, J 6, 1'-H$_2$), 2.71 (3H, s, 4-CH$_3$); m/z (%) 325 (100, M+1$^+$), 264 (63); $\nu_{max}$ (KBr disc)/cm$^{-1}$ 3396, 1616, 1574, 1564, 1304.

EXAMPLE 45

2-Chloroethyl 4-methyl-1H-[1]benzothieno[2,3-f]indole-2-carboxamide

2-Hydroxyethyl 4-methyl-1H-[1]benzothieno[2,3-f]indole-2-carboxamide (0.100 g, 0.31 mmol) was mixed with triphenylphosphine (0.160 g, 0.61 mmol) and carbon tetrachloride (8 ml) in DMF (1 ml). The mixture was heated to reflux for six hours and then allowed to cool to room temperature. The solvents were removed in vacuo to give an oil. Chromatography (eluting with 75% ethyl acetate/petrol) gave a brown solid . This was redissolved in ethyl acetate, the solution filtered and the solvent removed in vacuo to give the product as a yellow solid (0.073 g, 69%); δH [$^2$H$_6$]-DMSO 11.81 (1H, s, 1-NH), 8.82 (1H, t, J 5.5, amide N-H), 8.20–8.31 (1H, m, 9-H), 8.15 (1H, s, 10-H), 7.89–7.98 (1H, m, 6-H), 7.42–7.51 (2H, m, 7-H, 8-H), 7.34 (1H, s, 3-H), 3.79 (2H, t, J 5.5, 2'-H$_2$), 3.65 (2H, quartet, J 5, 1'-H2), 2.70 (3H, s, 4-CH$_3$); m/z (%) 342 (26, M$^+$), 306 (100), 263 (92), 235 (82); $\nu_{max}$ (KBr disc)/cm$^{-1}$ 3290, 1657, 1539.

ASSAYS FOR COMPOUND ACTIVITY

Assays for cell proliferation/cytotoxity were carried out in tissue culture grade 96 well microtitre plates (Costar). Cells in log growth were added to the plates at a concentration of 1×10$^3$ cells per well on day 0 and serially diluted compounds were then added on day 1. Plates were then incubated at 37° C. in 5% CO$_2$ in air for a further 4 days.

For quantitation of cell growth, the methylene blue biomass staining method was used, the test being read on a Multiscan plate reader at wavelength of 620 nm. The morphology of the cells was checked microscopically under phase-contrast immediately before the fixation and staining with methylene blue, and by ordinary light microscopy thereafter. IC50 values for active compounds were obtained using the computer programme, GS1 and dose-response slopes were also plotted.

When compounds were tested for activity in a colony forming assay the methods used were identical to those described earlier except that serially diluted compound was added to the sloppy agar when the test was set up, and replenished at the same concentration on day 7. The test results were read on day 14.

RESULTS

Comparative Growth and Morphology of HT1080scc2 and HT10801c

Growth rates in terms of cell number were similar for both lines to day 4 but thereafter HT1080scc2 cells continued to divide to reach saturation densities approximately 2 to 3 times higher than HTT10801c by day 5.

Phenotypic differences between the 2 lines were clearly evident. HT10801c cells displayed a much flatter morphology than the transformed cells and only a few mitotic cells were seen in confluent areas of the cultures. HT1080scc2 cells however continued to divide with numerous mitotic cells visible after confluence.

Grown under anchorage independent conditions in soft agar, HT1080scc2 produced several large colonies whereas HT10801c cells failed to produce any colonies greater than 0.1 mm in diameter.

Effects of Selected Compounds

A number of compounds of the invention were evaluated against the cell lines.

The compounds of the invention exhibited low toxicity with IC50 values in the range 50–100 μM.

The results of the "flattening" assay for compounds of cell invention are shown below:

| Compound | SSC2 Minimum flattening conc. (μM) |
|---|---|
| Example 1 | a |
| Example 2 | a |
| Example 3 | a |
| Example 4 | a |
| Example 5a | b |
| Example 5b | a |
| Example 6 | a |
| Example 7 | b |
| Example 8 | a |
| Example 9 | b |
| Example 10 | b |
| Example 11 | b |
| Example 12 | b |
| Example 13 | a |
| Example 14 | b |
| Example 15 | a |
| Example 16 | b |
| Example 17 | a |
| Example 18 | b |
| Example 19 | b |
| Example 20 | b |
| Example 21 | b |
| Example 22 | a |
| Example 23 | b |
| Example 24 | a |
| Example 25 | b |
| Example 26 | b |
| Example 27 | a |
| Example 28 | a |
| Example 29 | b |
| Example 30 | a |
| Example 31 | b |
| Example 32 | b |
| Example 33 | b |
| Example 34 | b |
| Example 35 | b |
| Example 36 | a |
| Example 37 | b |
| Example 38 | — |
| Example 39 | b |
| Example 40 | — |
| Example 41 | a |
| Example 42 | a |
| Example 43 | — |
| Example 44 | a |
| Example 45 | — | key:
a ≦ 25 μm
b ≦ 1 μm

The compounds are effective at achieving "flattening" ie de-transformation, at levels significantly below their toxicity level.

We claim:

1. A compound of the formula (I)

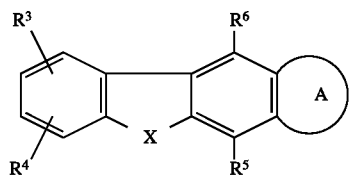

and salts and physiologically functional derivatives thereof, wherein A is

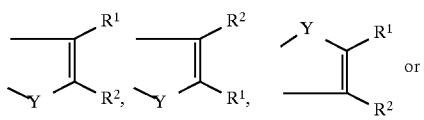 or 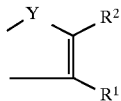

X is O, S, SO, $SO_2$, $CH_2$, CO or $NR^7$ wherein $R^7$ is H, $C_{1-10}$ alkyl, aralkyl containing from 1 to 4 atoms in the alkyl portion the aryl portion being a carbocyclic or heterocyclic aryl group, aryl selected from the group consisting of a carbocyclic aryl group and a heterocyclic aryl group containing a maximum of 10 ring atoms, alkenyl, $C_{1-10}$ acyl, alkynyl, sulphonyl or substituted sulphonyl;

Y is O, S, SO, $SO_2$, $CH_2$, CO or $NR^7$, with the proviso that Y is not O when X is O;

$R^1$ is $COOR^8$, $CONHR^8$, $CONR^8R^9$, $CSOR^8$, $CSSR^8$, $COSR^8$, $CSNHR^8$, $CSNR^8R^9$, $CNHOR^8$, wherein $R^8$ and $R^9$ are independently $C_{1-10}$ unsubstituted or substituted hydrocarbyl group which does or does not contain one or two oxygen atoms in the chain; the hydrocarbyl group being selected from the group consisting of straight-chain or branched $C_{1-10}$ alkyl, alkenyl, alkynyl, cycloalkyl, cycloalkenyl, cycloalkynyl, aralkyl containing from 1 to 4 carbon atoms in the alkyl portion and the aryl portion being a carbocyclic or heterocyclic group containing a maximum of 10 ring atoms, aralkenyl and aralkynyl groups where the $C_{1-10}$ alkyl, alkenyl or alkynyl portion is straight-chain or branched; said hydrocarbyl groups are unsubstituted or substituted by hydroxy, azido, alkenyl, halo, hydroxy, nitro, amino, alkylamino unsubstituted or substituted by one or two alkyl groups, cyano, carboxylate, alkyl ester, aralkyl ester, aryl ester wherein the alkyl ester, aralkyl ester and aryl ester are unsubstituted or substituted, alkyl, aryl, aralkyl, aryloxy, arylalkoxy, substituted arylalkoxy, sulphinyl, sulphonyl, thio, alkylthio, alkoxy, hydroxyalkyl, halo, alkyl, phosphate, phosphonate, silyl, silyloxy, wherein silyl and silyloxy are unsubstituted or substituted by one or more $C_{1-4}$ alkyl or aryl, keto, formyl; any substituent present on alkyl esters, aralkyl esters and aryl esters being nitro, amino, hydroxy, alkoxy, halogen, cyano and alkyl or $R^8$ and $R^9$ are independently alkoxyalkyl, heterocycloalkyl containing between 3 and 6 ring atoms, heteroaralkyl, or $R^8$ and $R^9$ are a sugar group, with the proviso that $R^1$ is not $COOR^8$, $CONHR^9$, $CONR^9R^{10}$ wherein $R^8$ is alkyl or aralkyl, $R^9$ and $R^{10}$ are alkyl, $R^2$ is H, halo, cyano, $COOR^8$, $C_{1-10}$ alkyl, aryl, selected from the group consisting of a carbocyclic aryl group and a heterocyclic aryl group containing a maximum of 10 ring atoms, alkenyl, alkynyl, alkoxy, wherein alkyl, aryl, alkenyl, alkynyl and alkoxy are unsubstituted or substituted or $CH_2CH_2CO_2R^{12}$ wherein $R^{12}$ is $C_{1-10}$ alkyl or aryl selected from the group consisting of a carboxycyclic aryl group and a heterocyclic aryl group containing a maximum of 10 ring atoms, $R^3$ and $R^4$ are independently H, hydroxy, $C_{1-10}$ alkyl, haloalkyl, alkoxy, halo, cyano, nitro, amino, alkyl amino, dialkyl amino, substituted $C_{1-10}$ alkyl, carboxyl or $CO_2R^{12}$, $R^5$ is H, $C_{1-10}$ alkyl, aralkyl containing from 1 to 4 atoms in the alkyl portion and the aryl portion being a carbocyclic or heterocyclic aryl group, nitro, amino, halo, cyano or CHO; and R⁶ is H, aryl selected from the group consisting of a carbocyclic aryl group and a heterocyclic aryl group containing a maximum of 10 ring atoms, $C_{1-10}$ alkyl, aralkyl containing from 1 to 4 atoms in the alkyl portion and the aryl portion being a carbocyclic or heterocyclic aryl group, nitro, halogen, CHO or COR¹³ wherein R¹³ is $C_{1-10}$ or aryl selected from the group consisting of a carbocyclic aryl group and a heterocyclic aryl group containing a maximum of 10 ring atoms.

2. A compound as claimed in claim 1, wherein R⁸ is a sugar and this group is present in a protected or unprotected form.

3. A compound as claimed in claim 1 having the formula (VI)

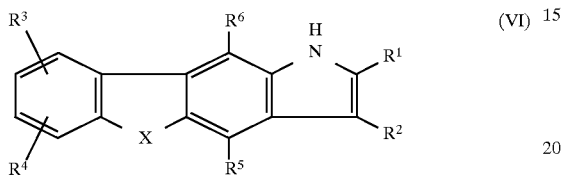

wherein,
X is S, O or NH;
R¹ is COOR⁸, where R⁸ is a group of formula

—(CH₂COO)ₙZ where n is 0 or 1 and
Z is a phenyl or benzyl group optionally substituted by one or more groups selected from hydroxy, carboxyl, nitro, amino, phthalimido, p-nitrobenzyl and p-nitrobenzyloxy;
or Z is a $C_{1-4}$ straight or branched alkyl group substituted by one or more groups selected from hydroxy, carboxyl, dialkylamino, alkylsulphinyl, alkylsulphonyl and benzyloxy;
or Z is a substituted glucofuranosyl moiety;
R² is H or $C_{1-10}$ alkyl; R³ is H, alkoxy, hydroxy or halo; R⁴ is H, alkoxy, hydroxy or halo; R⁵ is $C_{1-10}$ alkyl; and R⁶ is H; or salts thereof.

4. A compound, or a salt thereof, selected from:
[(2-Dimethylamino)ethyl]3,4-dimethylpyrrolo[3,2-b] carbazole-2-carboxylate;
(2-Methylsulphinylethyl)3,4-dimethylpyrrolo[3,2-b] carbazole-2-carboxylate;
(2-Methylsulphinylethyl)3,4-dimethylpyrrolo[3,2-b] carbazole-2-carboxylate;
(1,3-Dibenzyloxypropyl-2)3,4-dimethylpyrrolo[3,2-b] carbazole-2-carboxylate;
3-(4-Nitrophenylmethoxy)phenylmethyl 3,4-dimethylpyrrolo[3,2-b]carbazole-2-carboxylate;
3-(tert-Butyldiphenylsilyloxyphenyl)methyl 3,4-dimethylpyrrolo[3,3-b]carbazole-2-carboxylate;
(3-Hydroxyphenyl)methyl 3,4-dimethylpyrrolo[3,2-b] carbazole-2-carboxylate;
(1-Hydroxy-3-methylpropyl-2)3,4-dimethylpyrrolo[3,2-b]carbazole-2-carboxamide;
2-Hydroxyethyl 3,4-dimethylpyrrolo[3,2-b]carbazole-2-carboxamide;
2-Chloroethyl 3,4-dimethylpyrrolo[3,2-b]carbazole-2-carbooxamide;
N-(2-Aminoethyl)3,4-dimethylpyrrolo[3,2-b]carbazole-2-carboxamide;
N-(2-Acetamidoethyl) 3,4-dimethylpyrrolo[3,2-b] carbazole-2-carboxamide;
(3-Aminopropyl-1)3,4-dimethylpyrrolo[3,2-b]carbazole-2-carboxamide;
2-Hydroxyethyl 4-methyl-1H-[1]benzothieno[2,3-f] indole-2-carboxamide;
2-Chloroethyl 4-methyl-1H-[1]benzothieno[2,3-f]indole-2-carboxamide.

5. A pharmaceutical formulation which comprises a compound of formula (I) according to claim 1 together with a pharmaceutically acceptable carrier thereof.

6. A method of treatment of tumours in animals, which comprises the administration of an effective amount of a compound of claim 1 or a salt thereof.

7. A process of preparing an ester of the compound of claim 1 comprising reacting a compound of the formula

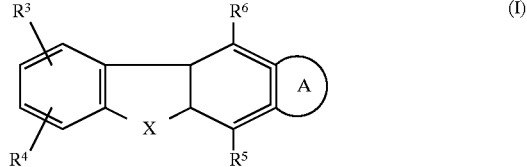

in which R¹ is COOR⁸ in which R⁸ is other than H, with an ester-forming group.

* * * * *